United States Patent [19]
Roizman

[11] Patent Number: 6,120,773
[45] Date of Patent: *Sep. 19, 2000

[54] RECOMBINANT HERPES SIMPLEX VIRUSES VACCINES AND METHODS

[75] Inventor: Bernard Roizman, Chicago, Ill.

[73] Assignee: Arch Development Corporation, Chicago, Ill.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/272,772

[22] Filed: Jul. 8, 1994

Related U.S. Application Data

[63] Continuation of application No. 07/579,834, Sep. 10, 1990, Pat. No. 5,328,688.

[51] Int. Cl.[7] .......................... A61K 39/245; C12N 7/04; C12N 7/00
[52] U.S. Cl. .................... 424/205.1; 424/231.1; 424/186.1; 435/235.1; 435/236; 536/23.72
[58] Field of Search .................... 424/231.1, 204.1, 424/229.1, 230.1, 93.2, 281.1, 205.1, 186.1, 225.1, 227.1; 435/235.1, 236, 69.1, 69.3; 536/23.72

[56] References Cited

U.S. PATENT DOCUMENTS

| | | | |
|---|---|---|---|
| 4,769,331 | 9/1988 | Roizman et al. | 435/69.1 |
| 4,859,587 | 8/1989 | Roizman et al. | 435/235.1 |
| 4,999,296 | 3/1991 | Kit et al. | 435/69.1 |
| 5,068,192 | 11/1991 | Cochran | 435/235.1 |
| 5,238,688 | 8/1993 | Roizman | 424/205.1 |

OTHER PUBLICATIONS

Location and Orientation of Homologous Sequences in the Genomes of Five Herpesviruses by A.J. Davison and N.M. Wilkie, *J. gen. Virol.* (1983), 64, 1927–1942.
MacLean et al, *J. Gen. Virol.* 72: 2305–2310, 1991.
Thompson et al, *Microb Pathog* 1: 409–16 (abstract only cited), Aug. 1986.
Thompson et al, *Virology* 172: 435–450, 1989.
Ackermann et al., *J. Virol.*, 58(3), 843–850 (1986).
Braun et al., *J. Virol.*, 46, 103–112 (1983).
Brown et al., *J. Gen. Virol.*, 18, 329–346 (1973).
Centifanto–Fitzgerald et al., *J. Exp. Med.*, 155, 475–489 (1982).
Chou et al., *Cell*, 41, 803–811 (1985).
Chou et al., *J. Virol.*, 57(2), 629–637 (1986).
Chou et al., *J. Virol.*, 64(3), 1014–1020 (1990).
Deiss et al., *J. Virol.*, 59 605–618 (1986).
Ejercito et al., *J. Gen. Virol.*, 2, 357–364 (1968).
Field et al., *J. Hygiene*, 81, 267–277 (1978).
Fields et al., Eds., *Fundamental Virology*, Chap. 10, 161–163 (1986).
Fields et al., Eds., *Field's Virology*, Chap. 66, 1843–1887 (1990).
Hammer et al., *J. Infect. Dis.*, 141(4), 436–440 (1980).
Hayward et al., *Proc. Natl. Acad. Sci. (USA)*, 72(11), 4243–4247 (1975).
Honess et al., *J. Virol.*, 12, 1347–1365 (1973).
Hubenthal–Voss et al., *J. Virol.*, 62, 454–462 (1988).
Javier et al., *J. Virol.*, 61(6), 1978–1984 (1987).
Kieff et al., *J. Virol.*, 8, 125–132 (1971).
Larder et al., *J. Gen. Virol.*, 67, 2501–2506 (1986).
Linnemann et al., *Lancet*, i. 964–966 (1978).
McGeoch et al., *J. Gen. Virol.*, 69, 1531–1574 (1988).
McGeoch et al., *Nucleic Acids Res.*, 14, 1727–1745 (1986).
Meignier et al., *J. Infect. Diseases*, 158(3), 602–614 (1988).
Meignier et al., *Vaccines 87*, Cold Spring Harbor Laboratory, 368–373 (1987).
Meignier et al., *Virology*, 162, 251–254 (1988).
Mocarski et al., *Cell*, 31, 89–97 (1982).
Mocarski et al., *Proc. Natl. Acad. Sci. (USA)*, 78, 7047 (1981).
Morse et al., *J. Virol.*, 26(2), 389–410 (1978).
Perry et al., *J. Gen. Virol.*, 67, 2365–2380 (1986).
Perry et al., *J. Gen Virol.*, 69, 2831–2846 (1988).
Poffenberger et al., *J. Virol.*, 53(2), 587–595 (1985).
Poffenberger et al., *Proc. Natl. Acad. Sci. (USA)*, 80, 2690–2694 (1983).
Post et al., *Cell*, 25, 227–232 (1981).
Post et al., *Proc. Natl. Acad. Sci. (USA)*, 77(7), 4201–4205 (1980).
Sanger et al., *Proc. Natl. Acad. Sci. (USA)*, 74, 5463–5467 (1977).
Sheldrick et al., *Cold Spring Harbor Symp. Quant. Biol.*, 39, 667–678 (1975).
Stevens et al., *J. Exp. Medicine*, 133, 19–38 (1971).
Taha et al., *J. Gen. Virol.*, 70, 705–716 (1989).
Taha et al., *J. Gen. Virol.*, 70, 3073–3078 (1989).
Thompson et al., *J. Virol.*, 55(2), 504–508 (1985).
Thompson et al., *J. Virol.*, 58(1), 203–211 (1986).
Thompson et al., *Virology*, 131, 171–179 (1983).
Thompson et al., *Virology*, 131, 180–192 (1983).
Thompson et al., *Virology*, 172, 435–450 (1989).
Varmuza et al., *Cell*, 41, 793–802 (1985).
Vlazny et al., *Proc. Natl. Acad. Sci. (USA)*, 79, 1423–1427 (1982).
Wadsworth et al., *J. Virol.*, 15(6), 1487–1497 (1975).
Warren et al., *NEJM*, 298:1068–1070 (1978).
Civil Complaint filed Jul. 8, 1999 in the United States District Court for the Northern District of Illionis Eastern Division; Joany Chou (Plaintiff) v. The University of Chicago, Arch Development Corporation, Bernard Roizman and Aviron Company (Defendants); Civil Action No. 99C 4495.

*Primary Examiner*—Mary E. Mosher
*Attorney, Agent, or Firm*—Marshall, O'Toole, Gerstein, Murray & Borun

[57] ABSTRACT

A recombinant herpes simplex virus genome having modified $\gamma_1 34.5$ genes incapable of expressing an active ICP34.5 gene product, vaccines comprising the recombinant herpes simplex virus genome methods for immunizing a host against the herpes simplex virus using the recombinant herpes simplex virus genome, and a method for preparing the vaccine are disclosed.

28 Claims, 20 Drawing Sheets

```
                                                    DR1
F:    TTTAAAGTCG CGGCGGC--GCA GCCCGGGCCC CCGGCGGGCCG AGACGAGCGA GTTAGACAGG    60
17:             CG        T                                     T
MGH:            CAC       -A                                    T
CVG:            CGC       -                                     T

F:    CAAGCACTAC TCGCCTCTGC ACGCACATGC TTGCCTGTCA AACTCTACCA CCCCGGCACG      120

F:    CTCTCTGTCT CCATGGCCCG CCGCCGCCGC C--ATCGGGCC CCGCCGCCC CCGGCCGCCC       180
MGH:                                                  GCC
CVG:                                                  GCC
```

FIG. 1A

```
F:    GGGCCCACGG GGGCCGTCCC AACCGCACAG TCCCAGGTAA CCTCCACGCC CAACTCGGAA  240
17:                         G
MGH:                        G
CVG:

F:    CCCGCGGTCA GGAGCGGCGCC CGCGGCCCGCC CCGCCCGCC CCCCCGCCAG TGGGCCCCCG  300
17:            T                                              G
MGH:           T                          ----------          G
CVG:                                                          G

F:    CCTTCTTGTT CGCTGCTGCT GCGCCAGTGG CTCCACGTTC CCGAGTCCGC GTCCGACGAC  360
17:                        G
MGH:                                     G         G
CVG:                                                G         G
```

FIG. 1B

```
                                                                                    420
F:    GACGATGACG ACGACTGGCC GGACAGCCCC CCGCCCGAGC CGGGCGGCCAGA GGCCCCGGCCC
17:                                              T
MGH:
CVG:

480
F:    ACCGCCGCCG CCCCCCGCCC CC-GGTCCCC-A CCGCCCCGGGCG CGGGGCCCGGG GGGGCGGGGCT
17:                          C G    C                    T               A
MGH:                         -  -    -                    -
CVG:                         -  -    -

540
F:    AACCCCTCCC ACCCCCCCTC ACGCCCCTTC CGCCTTCCGC CGCGCCTCGC CCTCCGCCTG
17:   G                     G
MGH:
CVG:  G
```

FIG. 1C

```
                                                                600
F:    CGCGTCACCG CAGAGCACCT GGGCGGCCTG CGCCTGCGAC GCGCGGGGCGG GGAGGGGGCG
17:
MGH:                     G
CVG:                     G

*          *          *          *     660
F:    CCGGAGCCCC CCGGCGACCCC CGGCGACCCCC CGGCGACCCCCG CGACCCCCG DACCCCCGCG
17:
MGH:
CVG:                                                            ---------

*          *          *          *            720
F:    ACCCCCGGCGA CCCCCGGCGAC CCCCGGCGACCC CCCGGCGACCC CCGGCGGGT GCGCTTCTCG
17:          ---------- ---------- ---------- ----------
MGH:         ---------- ---------- ---------- ----------
CVG:         ---------- ---------- ---------- ----------
```

FIG. 1D

```
F:            CCCCACGTCC GGGTGCGCCA CCTGGTGGTC TGGGCCTCGG CCGCCCGCCT GGGCGCGCCGC
17:                                                                            780
MGH:
CVG:

F:            GGCTCGTGGG CCCGCGAGCG GGCCGACCGG GCTCGGTTCC GGGCGCGGGT GGGGGAGGCC
17:                                                                            840
MGH:
CVG:

F:            GAGGCGGGTCA TCGGGACCGTG CCTGGGGCCC GAGGCCCGTG CCCGGGCCCT GGCCCGCGGA
17:                                                                            900
MGH:                    C          A                                  C
CVG:
```

FIG. 1E

```
F:   GCCGGGCCCGG CGAACTCGGT CTAACGTTAC ACCCGAGGCG GCCTGGGTCT TCCGCGGAGC
17:                                    —
MGH:
CVG:
                                                                   960

F:   TCCCGGGAGC TCCGCACCAA GCCGCTCTCC GGAGAGACGA TGGCAGGAGC CGGGCATATA
17:
MGH:                                A
CVG:                                A
                                                                  1020

F:   TACGCTGGGA GCCGGCCCGC CCCC--GAGGCG GGCCCGCCCT CGGAGGGCGG GACTGGCCAA
17:           T            T ACAG                            - - -
MGH:          A
CVG:          A
                                                                  1080
```

FIG. 1F

```
F:   TCGGGCGGCCG CCAGCGCGGGC GGGGCCCGGC CAACCAGCGT CCGCCGAGTC TTCGGGGCCC
17:                                                                    1140
MGH:                                                              G
CVG:                                                              G

F:   GGCCCCACTGG GCGGGAGTTA CCGCCCAGTG GGCCGGGCCG CCCACTTCCC GGTATGGTAA
17:              T                     A                                1200
MGH:              T AC C
CVG:              T AC C

F:   TTAAAAACTT ACAAGAGGCC TTGTTCCGCT TCCCGGTATG GTAATTAGAA ACTCATTAAT
17:                                                                    1260
MGH:   G
CVG:   G
```

FIG. 1G

```
                                                                                    1320
F:
17:   GGGCGGCCCC GGCCGCCCTT CCCGCTTCCG GCAATTCCCG CGGCCCTTAA TGGGCAACCC
MGH:
CVG:

1335
F:
17:   CGGTATTCCC CGCCT
MGH:
CVG:
```

FIG. 1H

MET ALA ARG ARG ARG ARG --- HIS ARG GLY PRO ARG ARG ARG PRO ARG PRO GLY PRO THR GLY 20
                              ARG
                              ARG

ALA VAL PRO THR ALA GLN SER GLN VAL THR SER THR PRO ASN SER GLU PRO ALA VAL ARG SER 41
                                                                          VAL
                                                                          VAL

ALA PRO ALA ALA ALA PRO PRO PRO PRO ALA SER GLY PRO PRO SER CYS SER LEU LEU 62
                                        GLY
                                    ----GLY
                                        GLY

LEU ARG GLN TRP LEU HIS VAL PRO GLU SER ALA SER ASP ASP ASP ASP ASP ASP TRP PRO 83
                GLN

```
                                                                             104
Asp Ser Pro Pro Pro Glu Pro Ala Pro Glu Ala Arg Pro Thr Ala Ala Ala Pro Arg Pro
                                                 Ser

125
Ser Pro Pro Gly Ala Gly Pro Gly Gly Ala Asn Pro Ser His Pro Pro Ser Arg Pro
Gly Pro His Arg Pro Ala Trp Ala Arg Gly Leu Thr Pro Thr Pro Pro Arg Ala

Asp                               146
Phe Arg Leu Pro Pro Arg Leu Ala Leu Arg Val Thr Ala Glu His Leu Ala Arg Leu
Pro Ser Ala Phe Arg Arg Ala Ser Pro Ser Ala Cys Ala Ser Pro Arg Ser Thr Trp Arg Ala

*                                       *167
Arg Leu Arg Arg Ala Gly Gly Glu Pro Ala Pro Ala Thr Pro Ala
Cys Ala Cys Asp Ala Arg Ala Gly Arg Ser Pro Pro Arg Pro Arg Ala
                             Lys

*                                           *                        *188
Thr Pro Ala Thr Pro Ala ---  ---  ---  Thr Pro Ala Thr Pro Ala
Arg Pro Pro Arg Pro ---  ---  ---        Arg Pro Arg Pro Pro
```

```
THR PRO ALA ARG VAL ARG PHE SER PRO HIS VAL ARG VAL ARG HIS LEU VAL VAL TRP ALA SER  209
--- --- PRO ARG GLY CYS ALA SER ARG THR SER GLY CYS ALA PRO THR TRP TRP SER GLY PRO

ALA ALA ARG LEU ALA ARG GLY SER TRP ALA ARG ALA ASP ARG ALA ARG PHE                  230
ARG PRO PRO ALA TRP ARG ALA ALA ARG GLY PRO ALA SER PRO THR GLY LEU GLY SER

ARG VAL ALA GLU ALA VAL ILE GLY PRO CYS LEU GLY PRO GLU ALA ARG ALA ARG              251
GLY ALA GLY TRP ARG ARG PRO ARG SER GLY ARG ALA TRP GLY PRO ARG PRO VAL PRO
                                                                    LYS

ALA LEU ALA ARG GLY ALA GLY PRO ALA ASN SER VAL Oc                                   263
GLY PRO TRP PRO ALA GLU PRO ALA ARG ARG THR PRO GLU ALA ALA TRP
SER ASN VAL THR PRO GLU ALA ALA TRP
ARG SER ARG ARG THR PRO GLU ARG ARG TRP GLN GLU

VAL PHE ARG GLY ALA PRO GLY SER SER ARG SER PRO GLU ARG ARG TRP GLN GLU
PRO ARG ILE TYR THR LEU GLY ALA SER PRO PRO SER GLN GLY GLY PRO ARG GLY ARG ASP
```

FIG. 2C

Trp Pro Ile Gly Gly Arg Gln Arg Gly Gly Ala Arg Pro Thr Ser Val Arg Arg Val Phe Gly

Ala Arg Pro Ile Gly Arg Glu Leu Pro Pro Asn Gly Pro Arg Pro Leu Pro Gly Met Val

Ile Lys Asn Leu Gln Glu Ala Leu Phe Arg Phe Pro Val Trp Oc

FIG. 2D

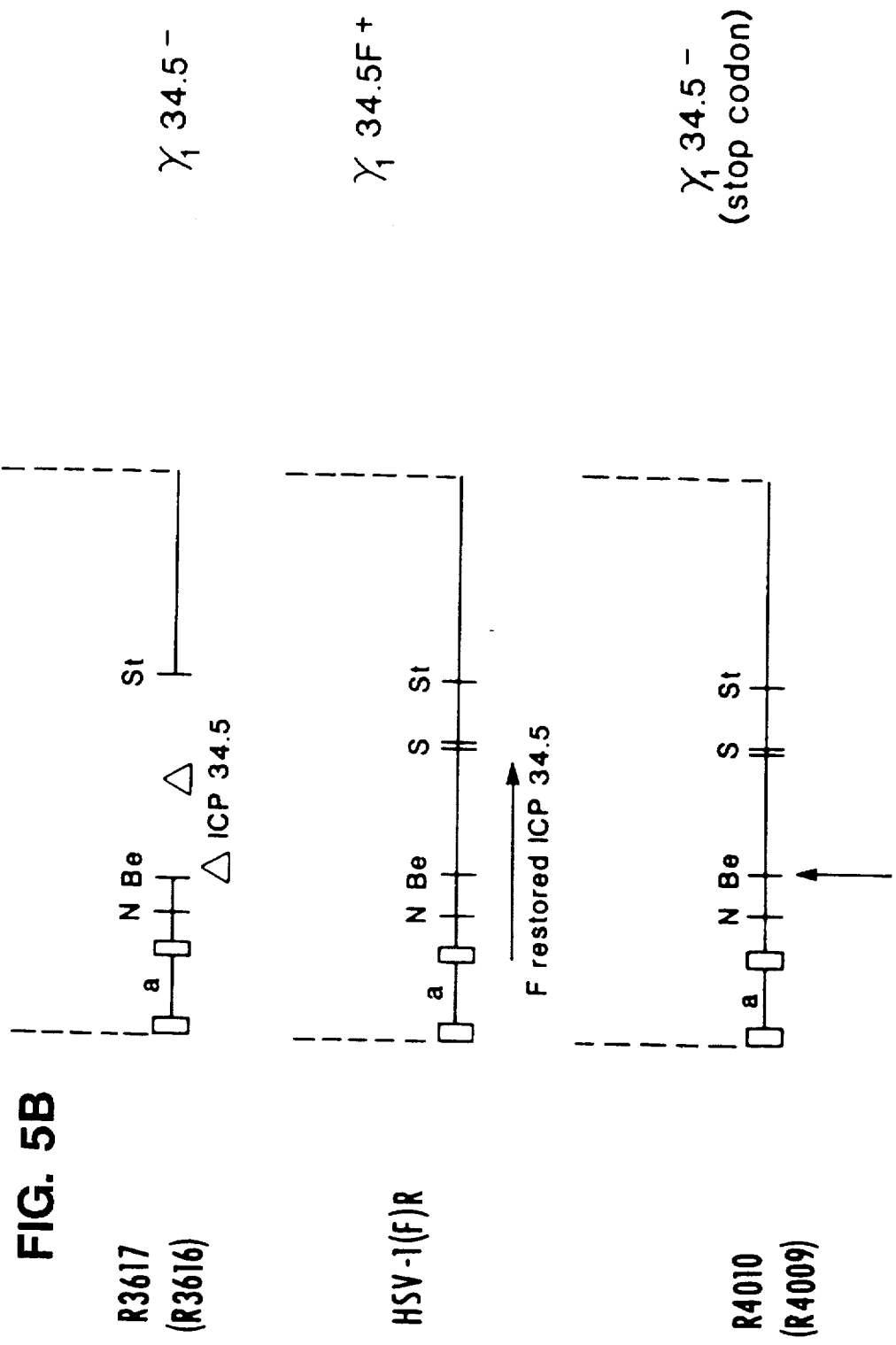

```
GTAACCTAGACTAGTCTAGC*****
*****GATCTGATCAGATCGCATTG
```

R4004
(R4003)

```
MetAspGluTyrAspAspAlaAspProAlaLeuAlaAlaLeuAlaGlyLeuTyrAspProArgAlaAlaProGlyMet
CATGGACGAGTACGACGACGAGTACGAGGCGACGCCGACGCCGAGCGCCGCCGCCGGGCCCCGGG*****
****CTGCTCATGCTGCTGCTCGTGCTGCGGCTGCGGCCCGGGGCCCCGGGGCCCGTAC
```

Tag Insertion

FIG. 5C

RECOMBINANT HERPES SIMPLEX VIRUSES VACCINES AND METHODS

CROSS-REFERENCE TO RELATED APPLICATION

This is a continuation of commonly assigned application Ser. No. 07/579,834 filed Sep. 10, 1990, now U.S. Pat. No. 5,328,688 issued Jul. 12, 1994.

BACKGROUND

The present invention relates in general to recombinant virus strains, live viral vaccines, methods for making the strains and vaccines, and methods for immunizing a host against a virus. More specifically, the present invention relates to recombinant herpesvirus strains, live viral vaccines incorporating such strains, methods for making such strains and vaccines, and methods for immunizing a human host against herpes simplex virus using the vaccines wherein a vaccinal viral DNA does not encode an active ICP34.5 gene product, such as a herpesvirus having a deletion or a stop codon in reading frame within a coding region in all copies of the ICP34.5 gene.

Viruses may cause infected cells to produce specific proteins. These proteins interact with each other and with cellular proteins and with viral nucleic acids to cause viral progeny to be made, to destroy the infected cell and to spread infection to previously noninfected cells. Some of these proteins also stimulate a host immune response, which may permit the viruses encoding them to be useful as a component of a viral vaccine.

Herpes simplex virus (HSV) is a relatively common human pathogen which can cause fatal disease in the young or immunosuppressed.

There are two distinct serotypes, herpes simplex virus type 1 ("HSV-1") and herpes simplex virus type 2 ("HSV-2"), respectively associated with fever blisters and genital lesions. HSV-1 and HSV-2 are related immunologically, but most of their proteins carry distinguishing characteristics which allow them to be differentiated. See, Morse et al., *J. Virol.*, 26(2), 389–410 (1978), the disclosure of which is incorporated herein by reference.

HSV is characterized by the ability to establish latent infections in the central nervous system ("CNS") of its host, specifically the neural ganglia [Stevens et al., *J. Exp. Medicine*, 133, 19–38 (1971)). This tropism for the CNS may result in encephalitis [Whitley, *Virology*, 2nd ed., Fields et al., eds., Raven Press, New York, 1843–1887 (1990)].

Several regions of the HSV genome may relate to viral neurovirulence. These regions include those containing the thymidine kinase gene [Field et al., *J. Hygiene*, 81, 267–277 (1978)] the DNA polymerase gene [Larder et al., *J. Gen. Virol.*, 67 2501–2506 (1986)], sequences within the internal repeats (Thompson et al., *J. Virol.*, 55(2), 504–508 (1985); Meignier et al., *J. Infect. Diseases*, 158(3), 602–614 (1988), and sequences between map units ("mu") 0.25 and 0.53 [Thompson et al., *J. Virol.*, 58, 203–211 (1986)]. A neural-specific, latency-associated transcript (LAT) in the long repeats may also be of interest, although there is no demonstrated function for the transcript thereof.

A virus strain useful in a vaccine against HSV-1 and HSV-2 may be avirulent, stable (i.e., does not revert to the virulent state), provide demonstrated immunity to massive challenges of wild type strains of both HSV-1 and HSV-2, have low pathogenicity, and be incapable of transforming host cells. It may be desirable for the vaccinal virus to disappear, or capable of reactivation, after immunization of a host, but in some cases it may be desirable for the virus to remain in a latent form in the host. This is best accomplished by a virus which contains only a small alteration in the genomic structure, thereby preserving the ability to replicate well outside the host while maintaining normal expression of immunity-inducing viral components.

Therefore, it is useful to obtain a stable, non-transforming live viral vaccine which either does not establish latent infections or which cannot be reactivated from a latent state, and which is effective against a herpes simplex virus.

SUMMARY OF THE INVENTION

A herpes simplex virus (HSV-1 or HSV-2) genome consisting essentially of an otherwise virulent herpes simplex virus which is avirulent for lacking only an ICP34.5 gene encoding an active gene product is provided according to the present invention. The herpes simplex virus may include an ICP34.5 gene having a stop codon in reading frame between a first and a last codon of a coding sequence of the ICP34.5 gene, and in particular may have a stop codon at a BstEII site in the ICP34.5 gene of HSV-1(F), such as the site in a presently-preferred herpes simplex virus designated R4009 (ATCC VR2278). Alternatively, the herpes simplex virus according to the present invention may include an ICP34.5 gene having a deletion mutation, more particularly, an ICP34.5 gene lacking a portion of a coding sequence between BstEII and StuI sites in HSV-1(F), which portion may be 1000 base pairs in length, such as in a herpes simplex virus according to the present invention which is designated R3616 (ATCC VR2280).

A vaccine including a herpes simplex virus genome is also provided according to the present invention. The genome consists essentially of a herpes simplex virus (HSV-1 or HSV-2) which is avirulent only for lacking an ICP34.5 gene encoding an active gene product, and is accompanied by a pharmaceutically acceptable diluent, adjuvant or carrier. In the vaccine, the herpes simplex virus may include an ICP34.5 gene having a stop codon in reading frame between a first and a last codon of a coding sequence of the ICP34.5 gene, particularly a stop codon at a BstEII site in the ICP34.5 gene of HSV-1(F), as in presently-preferred virus R4009 (ATCC VR2278). Alternatively, the herpes simplex virus in the vaccine may include an ICP34.5 gene having a deletion mutation, in particular a deletion of a portion of a coding sequence between BstEII and StuI sites in HSV-1(F), which deletion may be 1000 base pairs in length as in herpes simplex virus designated R3616 (ATCC VR2280).

A method for immunizing a human host against a herpes simplex virus according to the present invention includes a step of inoculating the host with an immunity-inducing dose of a vaccine including a herpes simplex virus genome consisting essentially of an otherwise virulent herpes simplex virus (HSV-1 or HSV-2) which is avirulent only for lacking an ICP34.5 gene encoding an active gene product, and a pharmaceutically acceptable diluent, adjuvant or carrier. The herpes simplex virus may include an ICP34.5 gene having a stop codon in reading frame between a first and a last codon of a coding sequence of the ICP34.5 gene, in particular a stop codon at a BstEII site in the ICP34.5 gene of HSV-1(F), such as is present in presently-preferred virus R4009 (ATCC VR2278). Alternatively, the herpes simplex virus may include an ICP34.5 gene comprising deletion mutation, in particular an ICP34.5 gene which lacks a portion, which may be 1000 base pairs in length, of a coding sequence between BstEII and StuI sites in HSV-1(F), such as in virus R3616 (ATCC VR2280).

A method for preparing a herpes simplex virus (HSV-1 or HSV-2) vaccine according to the present invention includes the steps of preventing transcription of an active product from an ICP34.5 gene an otherwise substantially intact herpes simplex vaccine virus, and combining said vaccine virus with a pharmaceutically acceptable carrier.

In the method for preparing a herpes simplex virus (HSV-1 or HSV-2) vaccine, the preventing step may include a step of deleting a portion of said ICP34.5 gene, and the deleting step may include the step of removing a coding sequence which may be 1000 base pairs in length between BstEII and StuI sites in HSV-1(F). Alternatively, the preventing step may include a step of inserting a stop codon in reading frame between a first and a last codon of a coding sequence of said ICP34.5 gene, and more particularly may include a step of introducing a stop codon at a BstEII site in the ICP34.5 gene of HSV-1(F).

BRIEF DESCRIPTION OF THE FIGURES

FIGS. 1A–1H illustrate a nucleotide sequences for a region of the genome which includes a gene encoding ICP34.5 in HSV-1 strains F, 17syn+, MGH-10 and CVG-2;

FIGS. 2A–2D illustrate deduced amino acid sequences encoded by the nucleotide sequences for the gene for ICP34.5 in HSV-1 strains F, 17syn+, MGH-10 and CVG-2 as illustrated in FIG. 1;

FIGS. 5A–5C are schematic representations of the genome of wild-type HSV-1 strain F and of recombinant viruses derived from it according to the present invention;

DETAILED DESCRIPTION

Figure 3A:
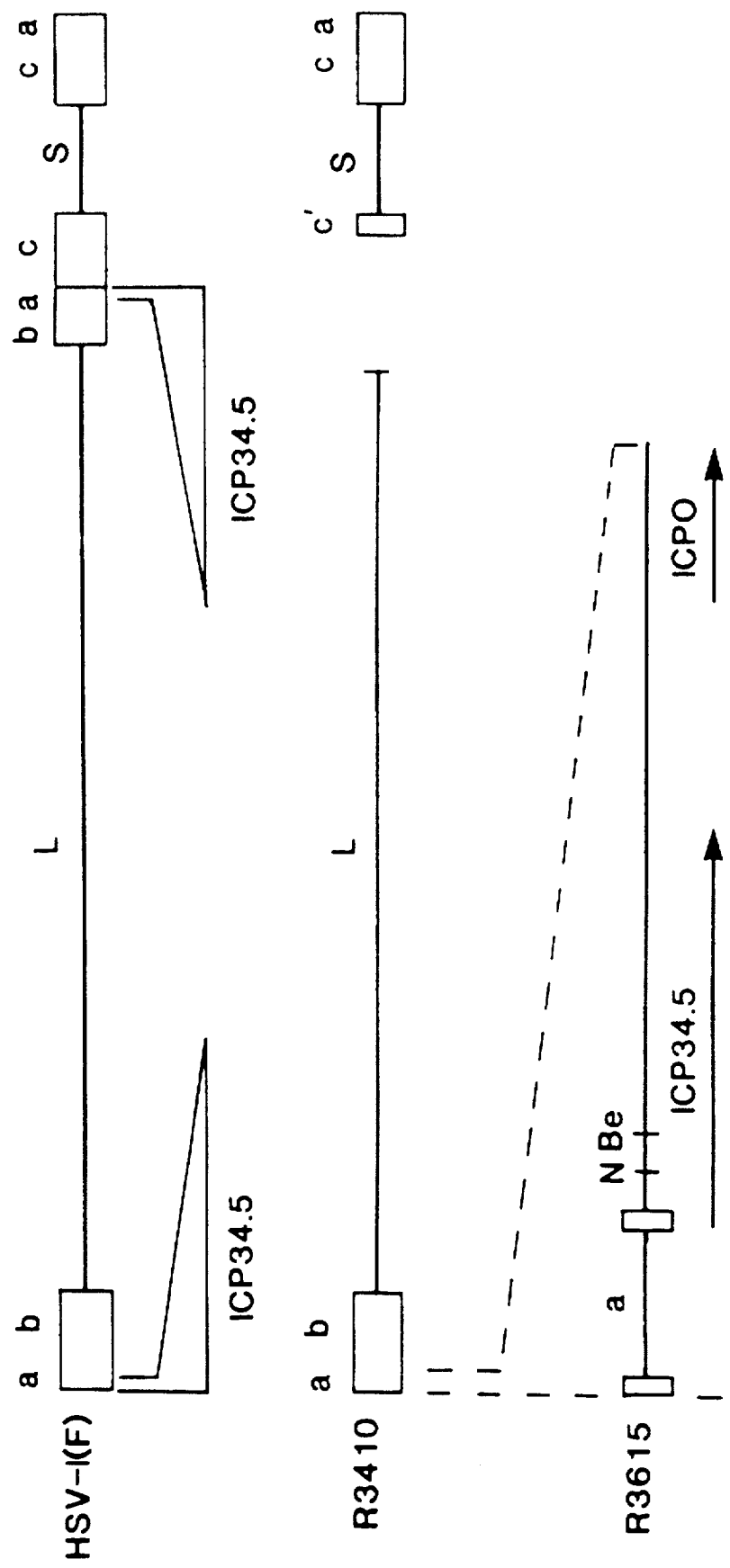
FIGS. 3A and 3B are schematic representations of nucleotide sequences in HSV-1(F) and recombinant viruses R3410, R3615 and R3976.

The structure of HSV DNA is described in the literature. See, e.g., Wadsworth et al., *J. Virol.*, 15(6), 1487–1497 (1975); Hayward et al., *Proc. Nat. Acad. Sci. (USA)*, 72(11), 4243–4247 (1975); and Morse et al., *J. Virol.*, 26(2), 389–410 (1978). Each of the HSV-1 and HSV-2 genomes consists of two, covalently-linked components, designated L and S. Each component consists of unique sequences ($U_L$ for the L component, $U_S$ for the S component) flanked by inverted repeats. The inverted repeats flanking the L components are designated ab and b'a'. The inverted repeats of the S components are designated as a'c' and ca.

In the HSV-1 genome, the long unique sequence is flanked by 9 Kbp inverted repeats designated as ab and b'a', respectively. A terminal 500 bp a sequence acts as a promoter characteristic of "late" or "γ" HSV genes such as the $\gamma_1 34.5$ gene (referred to herein as the ICP34.5 gene, i.e., as the gene encoding infected cell protein 34.5) the coding sequences of which, located in the adjacent b sequences, specify a protein of 263 amino acids with an apparent molecular weight of 44,000 [Chou et al., *J. Virol.*, 57, 629 (1986); Ackermann et al., *J. Virol.*, 58, 843 (1986) and Chou et al., *J. Virol.*, 64 1014 (1990]. The protein contains 3 to 10 repeats of the amino acid sequence Ala-Thr-Pro [Chou et al., *J. Virol.*, 57, 629 (1986); Ackermann et al., *J. Virol.*, 58, 843 (1986) and Chou et al., *J. Virol.*, 64 1014 (1990)].

The ICP34.5 gene lacks a canonical TATAA box, and the a sequence, its 5' transcribed non-coding domain, is very GC rich, contains numerous repeats and lacks the features characteristic of HSV promoters [Mocarski et al., *Proc. Nat'l. Acad. Sci. (USA)*, 78, 7047 (1981); Mocarski et al., *Cell*, 31, 89 (1982) and Chou et al., *Cell*, 41, 80 (1985)]. The a sequence contains the signals and the site of cleavage of the unit length DNA molecule from newly synthesized head to tail concatemers of viral DNA [Mocarski et al., *Cell*, 31, 89 (1982); Chou et al., *Cell*, 41, 803·(1985); Deiss et al., *J. Virol.*, 59, 605 (1986); Varmuza et al., *Cell*, 41, 793 (1985) and Vlazny et al., *Proc. Nat'l. Acad. Sci. (USA)*, 79, 1423 (1982)]. Specifically, the cleavage occurs within a direct repeat which flanks the a sequence [Mocarski et al., *Cell*, 31, 89 (1982)]. The transcription of the $\gamma_1 34.5$ gene is initiated in this repeat [Chou et al., *J. Virol.*, 57, 629 (1986)].

As described in Centifanto-Fitzgerald et al., *J. Exp. Med.*, 155, 475–489 (1982), the right terminus of the L component of HSV DNA contains genes the mutation of which leads to loss of neurovirulence as well as the inability to cause lesions in the cornea. These genes are reported to map approximately between 0.70 and 0.83, but their exact location was not identified before the present invention.

Poffenberger et al., *Proc. Natl. Acad. Sci. (USA)*, 80, 2690–2694 (1983), and Poffenberger et al., *J. Virol.*, 53, 587–595 (1985), reports that the internal inverted repeats (b'a'a'c') are not essential for the growth of HSV-1 in cell culture. Specifically, a recombinant HSV-1 virus (designated I358, ATCC VR2122) is described in which a portion of the unique sequence at the right end of the L component as well as most of the inverted repeats at the junction between the L and S components in a prototype arrangement is replaced by a small DNA sequence derived from the HindIII O fragment, normally located in the left end of the L component, and the thymidine kinase (TK) gene. The deletion of approximately 13 Kbp of HSV-1 DNA from the inverted repeats of the L and S components in I358 indicates that this virus, or a derivative of this virus, may serve as a vector of HSV DNA or foreign DNA inasmuch as additional DNA sequences may be inserted without affecting the packaging of the genome.

I358 itself is not suitable as a vector primarily because of the duplication of the HindIII O sequences. Because the HindIII O sequences at the novel junction between the L and S component are direct repeats of the sequences contained in the HindIII O fragment at its natural locations, the sequences between the HindIII O repeats spontaneously delete, and defective genomes accumulate in infected cells and culture. However, defective genomes do not contain all viral genes. They require wild type genomes as "helpers." Because they compete for viral and cellular factors, they "interfere," i.e., they reduce the yield of standard genomes. Moreover, even if the I358 genome were to be reconstructed so as to remove the HindIII O sequences duplicated at the novel L-S component junction, it is not be clear whether genes responsible for neurovirulence of the virus are deleted.

Another method used to identify the functions associated with the long unique region is deletion analysis. Meignier et al., *J. Infect. Dis.*, 158, 602–614 (1988) reports the removal of 14.5 Kb of DNA spanning the internal repeats of HSV-1. The resulting gap is reported to be filled with DNA from the unique short region of HSV-2, including the glycoproteins gD, gG, and gI. The resulting virus, designated R7017, is reported to show an almost 10,000-fold reduction in neurovirulence upon intracranial injection [Meignier et al., *J. Infect. Dis.*, 158(3), 602–614 (1988)]. This virus and related constructions are also disclosed in Roizman, U.S. Pat. No. 4,859,587, which is continued as Ser. No. 07/378,017 and which is a continuation-in-part of Ser. No. 06/616,930, now abandoned but continued as Ser. No. 07/455,771 filed Dec. 28, 1989, now abandoned but continued as application Ser. No. 07/923,015 filed Jul. 30, 1992, now U.S. Pat. No. 5,288,641 issued Feb. 22, 1994.

In or around the long unique region, an intertypic recombinant (HSV-1 X HSV-2) designated RE6, is reported to be over one million times less virulent than either of its parents in Thompson et al., *Virology*, 131, 171–179 (1983). This virus is reported to contain sequences from both HSV-1 (67%) and HSV-2 (33%), of which the latter is reported to contribute the internal and terminal repeats of the long unique region [Thompson et al., *Virology*, 131, 171–179 (1983)]. RE6 is reported to be distinguishable from other non-virulent intertypic recombinants tested in that it grew normally at the physiologic host temperature (38.5° C.). The mutation of RE6 is reported to be rescued to 0.71 mu to 0.83 mu [Thompson et al., *Virology*, 131, 180–192 (1983)]. However, the use of gel-purified fragments in marker rescue experiments, as opposed to the use of cloned DNA, creates the possibility that results may be due to contaminating DNA fragments or UV-induced mutations. The use of cloned HSV-1 fragments are reported to show the region including the mutation to be involved with neurovirulence, implicating a specific site at 0.72 mu [Thompson et al., *J. Virol.*, 55(2), 504–508 (1985)]. The region is reported to be narrowed to include only 0.79 mu to 0.82 mu [Javier et al., *J. Virol.*, 61(6), 1978–1984, (1987)], 0.81 to 0.83 [Taha et al., *J. Gen. Virology*, 70, 705–716 (1989)], and to a 1.6 kb fragment mapping between 0.82 mu to 0.832 mu [Thompson et al., *Virology*, 172, 435–450 (1989)].

Javier et al., *J. Virol.*, 65, 1978 (1987) and Thompson et al., *Virology*, 172, 435 (1989) report that an HSV-1 X HSV-2 recombinant virus consisting largely of HSV-1 DNA but with HSV-2 sequences located at one terminus of the L component is avirulent, and that virulence is restored by rescue of the HSV-2 sequences with the homologous HSV-1 fragment. Taha et al., *J. Gen. Virol.*, 70, 705 (1989) and Taha et al., *J. Gen. Virol.*, 70, 3073 (1989) describe a spontaneous deletion mutant lacking 1.5 Kbp at both ends of the long component of a HSV-2 strain.

A number of genes lie in or around the long unique region of the genome, including the gene for ICP34.5, genes for the immediate early proteins α-0, α-4, α-27, and the sequences giving rise to LAT. The smallest rescuing fragment used by Thompson et al., *Virology*, 172, 435–450 (1989) is in the region which includes the ICP34.5 gene identified by [Chou et al., *J. Virol.*, 57, 629 (1986)]. However, it is reported that the virus strain from which the rescuing fragment was derived does not contain an open reading frame in this region [Perry et al., *J. Gen. Virol.*, 69, 2831–2846 (1988)]. It is also reported that the rescuing strain does not have the open reading frame, but that three other virus strains do contain an open reading frame with significant homology to a sequence, suggesting the existence of a genuine gene [Chou et al., *J. Virol.*, 64, 1014 (1990)]. An epitope from the α-4 polypeptide is reported to be inserted in ICP34.5 and to be useful for precipitating the resulting hybrid protein from infected cells [Chou et al., *J. Virol.*, 64, 1014 (1990)].

Centifanto-Fitzgerald et al., *J. Exp. Med.*, 155, 475 (1982) reports the transfer, by means of a DNA fragment, of a virulence marker from a virulent to an avirulent strain of HSV-1.

Because of heterogeneity in the parent virus population, the loss of virulence has not heretofore been unambiguously related to a specific deletion although a particular recombinant obtained by marker rescue may be more virulent than the corresponding deletion mutant. A specific gene or gene product has not heretofore been unambiguously identified at the mutated locus and no gene has been specifically linked to a virulence phenotype.

It is generally the case that the smaller the deletion, the more likely it is that the virus will multiply in a host while retaining its antigenic properties. The main immune response to HSV-2 and HSV-1 is directed against surface proteins of the virus. The surface proteins of the virus are viral glycoproteins inserted into the virion envelope and into the plasma membrane of infected cells. Currently at least 7 viral glycoproteins are known to be specified by HSV-1 and HSV-2. These are glycoproteins B, C, and H mapping in the L component and glycoproteins D, E, I and G mapping in close proximity to each other in the S component. Of these glycoprotein genes, glycoprotein D mapping in the S component and, to a smaller extent, glycoproteins B and C mapping in the L component induce neutralizing antibody and may induce immunity. The strongest neutralizing antibody may be induced by glycoprotein D. This glycoprotein, even by itself, induces some protection in experimental animal systems. Thus, it is desirable that a potential HSV vaccine virus retain antigenic properties.

It is also desirable that a potential HSV vaccine not contain transforming domains. Transforming domains are defined as those which confer upon recipient cells the ability to establish tumors on transplantation in experimental animals. The transforming regions in HSV-2 genome are mapped in the L component of HSV-2 DNA. The corresponding sequences of HSV-1 genome do not immortalize or confer malignant transforming properties to cells. The DNA fragment carrying the genes for glycoprotein D and G of HSV-2 does not contain sequences known to be able to transform cells in culture.

$TK^-$ viruses (i.e. viruses lacking a TK gene) have a reduced capacity to establish latent infections in experimental animals. The parent virus of I358 [designated HSV-1(F) Δ305, described in Poffenberger et al., *Proc. Nat'l. Acad. Sci.* (*USA*), 80, 2690–2694 (1983) and Poffenberger et al., *J. Virol.*, 53, 587–595 (1985), and deposited on Aug. 14, 1990 with the American Type Culture Collection, 12301 Parklawn Drive, Rockville, Md. under the accession number VR2279] does not establish latency in experimental animals and it is thus reasonable to expect that the derivatives of 1358 lacking the TK gene would also fail to establish latency. $TK^-$ viruses, although having reduced capacity to establish latency, may not confer protection.

EXAMPLE 1

Cloning and Sequencing of HSV-1 Strains

To establish the extent of variability of the open reading frame that encodes ICP34.5, the nucleotide sequences of three HSV-1 strains passaged a limited number of times outside a human host were compared.

The isolation and properties of HSV-1(F) are described in Ejercito et al., *J. Gen. Virol.*, 2, 357–364 (1968). HSV-1 (MGH-10) is isolated from a case of HSV encephalitis [Hammer et al., *J. Infect. Dis.*, 141, 436–440 (1980)] an isolate obtained from a patient in a pediatric intensive care unit at Cleveland General Hospital [Linnemann et al., *Lancet*, i, 964–966 (1978)]. Both viruses were passaged only once since they were received, and no more than three times since their isolation from the human hosts. The construction and structure of recombinant virus R3615 is reported elsewhere [Ackermann et al., *J. Virol.*, 58, 843–850 (1986)]. Transfection of the viral and plasmid DNAs on rabbit skin cells and selection of the recombinant viruses under bromodeoxyuridine on human 143 thymidine kinase-negative cells were done as described in Post et al., *Cell*, 25, 227–232 (1981).

McGeoch et al., *J. Gen. Virol.*, 69, 1531–1574 (1988) and Perry et al., *J. Gen. Virol.*, 67, 2365–2380 (1981) report on the complete nucleotide sequence of HSV-1 strain 17syn+ [HSV-1(17)syn+], noting that in that strain the open reading frame ascribed to ICP34.5 is thoroughly disrupted. HSV-1 (F) differs from HSV-1(17)syn+ in several characteristics. HSV-1(F) was isolated from a recurrent facial vesicle [Ejercito et al., *J. Gen. Virol.*, 2, 357–364 (1968)] and passaged a maximum of four times in cells in culture. HSV-1(F) retains the temperature sensitivity characteristic of many HSV-1 isolates passaged a limited number of times in cells in culture. HSV-1(17)syn+, reported in 1973 [Brown et al., *J. Gen. Virol.*, 18, 329–346 (1973)], is described as the progeny of a plaque-purified virus. The passage history of HSV-1(17)syn+ has not been described, but it apparently is a multipassage laboratory strain. It may be used as the parental (temperature-resistant) strain for generation of temperature-sensitive mutants.

Viral DNAs were prepared from virions that accumulated in the cytoplasm of infected VERO cells as previously described [Kieff et al., *J. Virol.*, 8, 125–132 (1971)]. The BamHI SP junction fragments containing the domain of the gene that specified ICP34.5 were cloned in pUC18 plasmids [Vieira et al., *Gene*, 19, 259–268 (1982)] by using HSV-1(F) sequences as probes in colony blot hybridization. Further subclonings were done as necessary to facilitate sequencing of different regions of the gene. The sequencing was done in part by using the dideoxy-chain termination method [Sanger et al., *Proc. Nat'l Acad. Sci. (USA)*, 74, 5463–5467 (1977)] and in part by using a Sequences DNA-sequencing kit (United States Biochemical Corp., Cleveland, Ohio) and [α-$^{32}$P]dATP (Dupont-NEN Research Products, Boston, Mass.). Various oligonucleotide primers used in sequencing were synthesized in an Applied biosystems (Foster City, Calif. 380D DNA synthesizer. Reactions using dGTP and dITP as substrates in chain elongation and termination as supplied by kit were used to resolve regions of sequences of high G+C content.

The nucleotide sequences of the 5'-transcribed noncoding and coding domains of the gene that specifies ICP34.5 in HSV-1(F), HSV-1(MGH-10), HSV-1(CVG-2) along with the reported sequence of HSV-1(17)syn+ [McGeoch et al., *J. Gen. Virol.*, 69, 1531–1574 (1988) and Perry et al., 69, 2831–2846 (1988)] are shown in FIGS. 1A–1H.

A comparison of the nucleotide sequences of HSV-1 strains F, 17syn+, MGH-10, and CVG-2 in the region of the gene for ICP34.5 is shown in FIGS. 1A–1H, and the predicted open reading frames for ICP34.5 in these strains is shown in FIGS. 2A–2D. Unless otherwise indicated by a new base (insert of A, C, G, or T), a new amino acid (three-letter code), or the absence of a base or amino acid (−), the sequences for strains HSV-1(17)syn+, HSV-1 (MGH-10), and HSV-1(CVG-2) were identical to the sequence for HSV-1(F). An asterisk indicates initiation of a repeat sequence of nine nucleotides or three amino acids. Direct repeat 1 ("DR1") designates the 20-base-pair repeat sequence flanking the α sequence. Sequences upstream of direct repeat 1 are contained within the α sequence. The number at end of each line indicates the relative position from nucleotide 1 in FIG. 1A or from amino acid 1 in FIGS. 2A–2D. The initiation and termination codons for the HSV-1(F) sequence are underlined.

The RNA transcribed across the domain of the gene that specific ICP34.5 is initiated within DR1 of the α sequence [Chou et al., *J. Virol.*, 57, 629–637 (1986)]. Methionine codon 1 in all HSV strains is 90 nucleotides downstream from DR1, and, in three strains, 17syn+, MGH-10, and CVG-2, this sequence is identical in length to that of the F strain and differs from it in only one nucleotide.

The differences among the strains within the domain of the gene are as follows. The 5'-noncoding domain of the gene that specifies ICP34.5 includes most of the α sequence. The α sequences of 17syn+, MGH-10 and CVG-2 contain a dinucleotide insert and vary in the nucleotide sequence in the UB domain of the α sequence. Whereas both F and 17 syn+ contain four Arg residues at amino acids 3 to 6, strains MGH-10 and CVG-2 contain the insert GCC, and encode five Arg residues at that position. MGH-10 lacks 21 nucleotides corresponding to the F strain amino acids (Ala-46-Pro-Pro-Pro-Pro-Pro-Ala-52) present in all other strains. The strain 17syn+ sequence contains two additional nucleotides not present in other strains. HSV-1(F) and all other strains contain the sequence GCC CCC-GGTCCCC-A at nucleotide positions 423 to 430, whereas the reported sequence for strain 17syn+ is GCCCCCCGGTCCCCCA. The net effects of insertion of the two nucleotides are frameshifts at amino acid positions 104 and 106. In strain 17syn+ there are additional insertions and deletions which occur outside the coding domain of the genes for ICP34.5 of other strains; these occur at positions corresponding to nucleotides 1044 to 1064 of strain F. With the exception of the missing 21 base pairs predicted to encode seven amino acids in MGH-10 and the additional arginine residue in MGH-10 and CVG-2, the differences among strains MGH-10, CVG-2, and F are minor. MGH-10 has a total of five nucleotide substitutions resulting in three amino acid differences. CVG-2 has 11 nucleotide substitutions resulting in five amino acid differences from F. The ICP34.5-coding domain in strain F contains 10 repeats of the sequence CCCCCGCGA, which encodes the trimer Ala-Thr-Pro. The numbers of repeats in the coding domains of the other strains are five for 17syn+ and six for strains MGH-10 and CVG-2. Because of the frameshift, the repeat sequence in strain 17syn+ translates as Pro-Arg-Pro. The open reading frame in HSV-1(F) is predicted to encode 263 amino acids, i.e., less than the otherwise-reported 358 amino acids [Chou et al., *J. Virol.*, 57, 629–637 (1986)].

A proposal that a gene exists which encodes ICP34.5 is related to the finding that the terminal α sequence in juxtaposition to a reporter gene is able to promote expression [Chou et al., *J. Virol.*, 57, 629–637 (1986)]. However, the DNA that encodes ICP34.5 is difficult to sequence because it is G+C rich and contains long stretches of guanines and cytosines. Moreover, the 5'-untranscribed domain of the gene does not contain a TATAA box and is contained entirely within the terminal α sequence that also contains numerous repetitive G+C-rich elements, unlike most HSV-1 genes [Chou et al., *J. Virol.*, 57, 629–637 (1986)].

If the open reading frame were expressed, the close proximity and overlap with the terminal α sequence may indicate that the gene product is involved in one of the several functions of the terminal α sequence [Chou et al., *Cell*, 41, 803–811 (1985); Deiss et al., *J. Virol*, 59 605–618 (1986); Mocarski et al., *Cell*, 31, 7047–7051 (1981); Mocarski et al., *Cell*, 31, 89–97 (1982); and Varmuza et al., *Cell*, 41, 793–802 (1985)]. Several laboratories [Centifanto-Fitzgerald et al., *J. Exp. Med.*, 155, 475–489 (1982); Javier et al., *J. Virol.*, 61 1978–1984 (1987) and Meignier et al., *J. Infect., Diseases*, 158, 602–615 (1988)] report the mapping of a locus at or near the inverted repeat region which attenuates the ability of HSV-1 to cause central nervous system disease in mice.

The gene that specifies ICP34.5 contains 263 codons conserved in all three limited-passage strains, but not in the reported sequence of the HSV-1(17)syn+ strain. Nonconservation of the open reading frame that specifies ICP34.5 in the reported sequence of HSV-1(17)syn+ [McGeoch et al., *J. Gen. Virol.*, 69, 1531–1574 (1986) and Perry et al., *J. Gen. Virol.*, 69, 2831–2846 (1988)] indicates that the sequenced virus may have accumulated mutations since its original isolation. Consistent with this view is the report in Taha et al., *J. Gen. Virol.*, 70, 3073–3078 (1989) reporting that a variant of HSV-2 strain HG52 lacks 1.5 kbp covering the domain of the gene that specifies ICP34.5. The virus grows but is avirulent (50% lethal dose, $>10^7$ PFU) in mice inoculated intracerebrally.

Although sequencing of the HSV-1 genome [McGeoch et al., *J. Gen. Virol.*, 69, 1531–1574 (1988); McGeoch et al., *Nucleic Acids Res.*, 14, 1727–1745 (1986) and Perry et al., *J. Gen. Virol.*, 69, 2831–2846 (1988)] is useful, the knowledge that the nucleotide sequence of the ICP34.5 gene in three HSV-1 strains, i.e., HSV-1(F), HSV-1(CVG2), and HSV-1(MGH10), differs significantly from the reported sequence of the corresponding HSV-1(17)syn+ gene raises the possibility that additional mutations have accumulated in other genes of HSV-1(17)syn+ and underscores the need to sequence regions of particular interest in more than one virus strain to ensure that the sequence approximates that of a wild-type virus and does not reflect accumulated mutations of serial passages outside a human host.

The role of the gene for ICP34.5 in determining the ability of a virus to multiply and destroy central nervous system tissue is of particular interest. Of the viruses examined, two have been extensively tested for virulence in mice. HSV-1 (F), isolated from a recurrent facial lesion, is of moderate virulence, with a 50% lethal dose of approximately 100 PFU by intracerebral inoculation of mice. In contrast, MGH-10, derived from a case of human encephalitis, has a 50% lethal dose of 1 to 5 PFU by the same route in identical mouse strains [Meignier et al., *J. Infect. Diseases*, 158, 602–614 (1988)].

EXAMPLE 2

Construction of Recombinant Plasmid pRB3976

The evidence that the open reading frame between the terminal a sequence and the open reading frame that encodes α0 specifies a protein and that this protein is made in lytically infected cells is based in part on the reactivity of infected-cell extracts with a polyclonal antibody to the synthetic oligonucleotide (Ala-Thr-Pro)$_{10}$-Cys.

Inasmuch as the divergence in the nucleotide sequence of strain HSV-(17)syn+ occurs before the predicted repeat Ala-Thr-Pro in HSV-1(F), it could be argued that the antibody to the trimer repeat reacts with a different protein containing such repeats. It could also be argued that truncation of the open reading frame in recombinant virus R3615 is coincidental with the selection of a variant virus containing fewer Ala-Thr-Pro repeats.

Figure 3B:
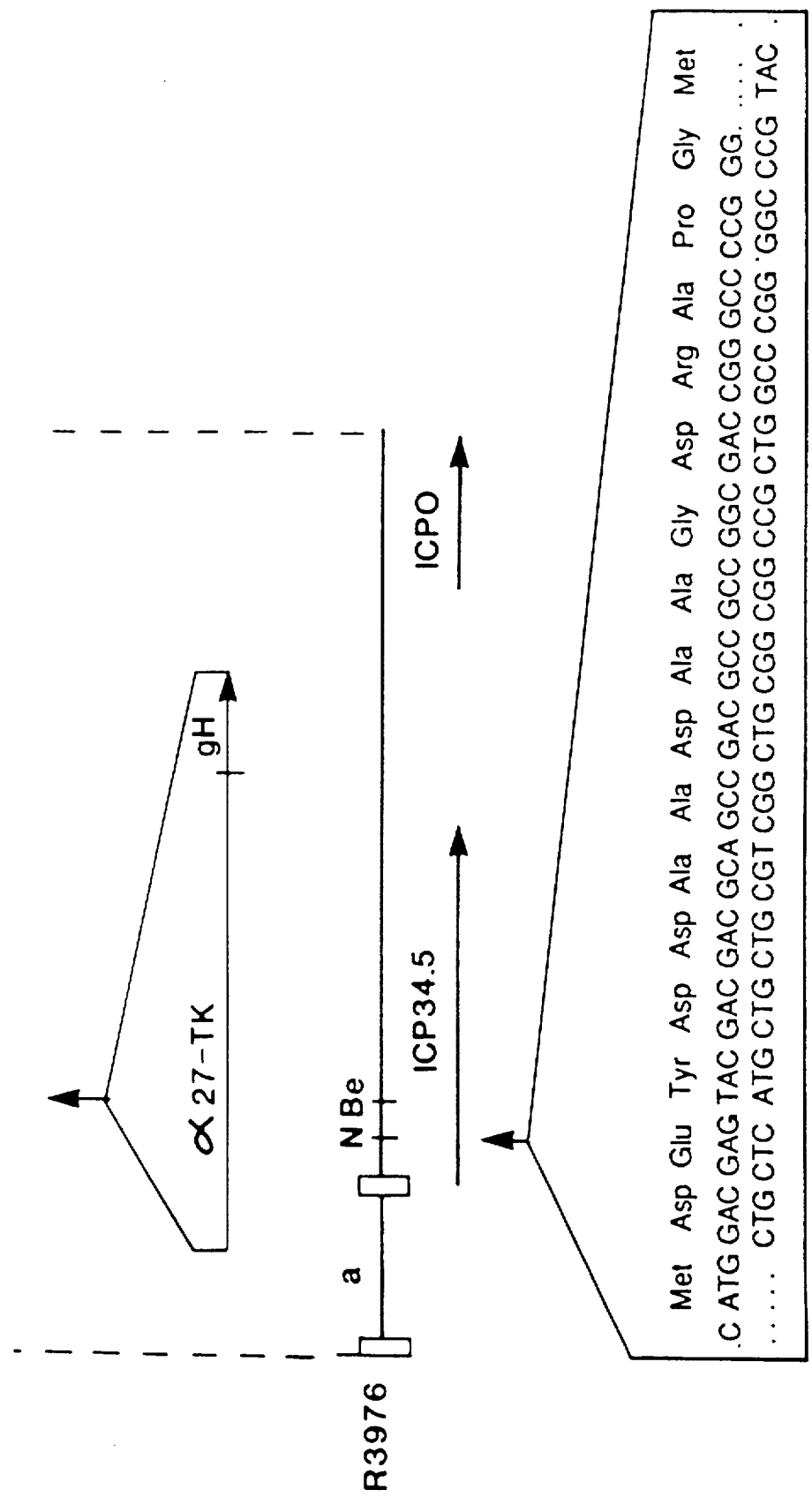

To demonstrate unambiguously that a rabbit polyclonal antibody to the repeat Ala-Thr-Pro reacts with the protein predicted to be encoded by the nucleotide sequence of HSV-1(F), an oligonucleotide that encodes the amino acids 121 to 135 containing an epitope of ICP4 in frame with the open reading frame at the NcoI site was inserted as illustrated in FIGS. 3A and 3B. Hubenthal-Voss et al., *J. Virol.*, 62, 454–462 (1988) reports that the synthetic polypeptide that encodes this sequence reacts with monoclonal antibody H943 to ICP4. The recombinant virus containing this epitope was designated R3976.

An oligonucleotide 50 bases long and its complement sequence designed to end in NcoI restriction enzyme cleavage sites were synthesized as described in Example 1 and as illustrated in FIGS. 3A and 3B.

The two oligonucleotides were then mixed at an equal molar ratio, heated to 80° C., and allowed to anneal by being cooled slowly to room temperature. The annealed DNA was then ligated to a cloned DNA fragment containing the gene for ICP34.5 and cleaved with NcoI. In the gene for ICP34.5, the NcoI site is located at the methionine initiation codon. The resulting plasmid, pRB3976, was sequenced (data not shown) to confirm the appropriate insertion as shown and then used in transfection experiments with the parental viral DNA. R3615, to generate recombinant virus R3976.

In FIG. 3A, within the sequence arrangement of HSV-1 (F), the a sequence identifies the terminal 500-base-pair sequence present in the direct orientation at the two genomic termini and in the inverted orientation at the junction between the L and S components of the genome [Sheldrick et al., Cold Spring Harbor Symp. Quanti. Biol., 39, 667–678 (1975) and Wadsworth et al., *J. Virol.*, 15, 1487–1497 (1975)]. b and c are large inverted repeats, 9 and 6 kbp length, respectively, which, flank the L and S components of the virus. In FIG. 3A, the extent of the deletion of sequences at the L-S component junction of recombinant virus R3410 is shown by the interrupted line [Ackermann et al., *J. Virol.*, 58, 843–850 (1986)].

In FIGS. 3A and 3B, within the sequence arrangement of R3615 showing insertion of an α27-tk chimeric gene into the BstEII site of the gene for ICP34.5, the insert contains at its terminus distal from the a sequence the regulatory domain, the 5'-transcribed noncoding domain, and the methionine initiation codon of glycoprotein H. The initiation codon was fused in frame with amino acid 27 of ICP34.5, generating a truncated form of this protein [Ackermann et al., *J. Virol.*, 58, 843–850 (1986)].

EXAMPLE 3

Electrophoresis of Cell Extracts

To ensure that the antibody to a predicted repeat sequence, Ala-Thr-Pro, reacted with ICP34.5 rather than with a heterologous protein with a similar repeat sequence, a short sequence of 45 nucleotides that encodes an epitope characteristic of another HSV-1 gene [Hubenthal-Voss et al., *J. Virol.*, 62, 454–462 (1988)] was inserted near the 5' terminus of the ICP34.5-coding domain.

In the sequence arrangement and construction of recombinant virus R3976 carrying the epitope encoded by ICP4 amino acids 121 to 135 [Hubenthal-Voss et al., *J. Virol.*, 62, 454–462 (1988)], the sequence that encodes these amino acids was inserted at the NcoI site of ICP34.5. At the bottom of FIG. 3B is the nucleotide sequence and predicted amino acid sequence of the insert on plasmid pRB3976 that was inserted into recombinant virus R3976 in frame with the gene for ICP34.5 that and which encodes the ICP4 epitope specifically recognized by monoclonal antibody H943.

Monolayer cultures containing $4 \times 10^6$ Vero cells were exposed to 5 to 10 PFU of recombinant viruses per cell for 2 hours. After adsorption, the inoculum was replaced with mixture 199 supplemented with 1% calf serum and maintained for 12 hours. The cells were then labeled with 10 μCi of [$^{35}$S]methionine (Dupont, NEN Research Products) in the same medium but without methionine for an additional 12 hours. The cells were then harvested, washed once with phosphate-buffered saline, pelleted by centrifugation at 4,000 rpm for 5 min and suspended in disruption buffer which consisted of 0.05 M Tris (pH 7.0), 8.5% (wt/vol) sucrose, 5% (vol/vol) 2 β-mercaptoethanol, and 2% (vol/vol) sodium dodecyl sulfate. Extracts were then boiled for 2 min in water, disrupted by sonication in a Branson Sonifier 200 (SmithKline, King of Prussia, Pa.) three times for 3 sec each time, and then subjected to electrophoresis in denaturing polyacrylamide gels.

The polypeptides were separated electrophoretically on denaturing 10% polyacrylamide gels, transferred electrically to nitrocellulose sheets, and reacted with rabbit antiserum R4 or monoclonal antibody H943 by using Vectastain ABC kits specifically for rabbit and mouse antibodies (Vector Laboratories Inc., Burlingame, Calif.) as previously described [Ackermann et al., *J. Virol.*, 58, 843–850 (1986) and Braun et al., *J. Virol.*, 46, 103–112 (1983)].

Figure 4:
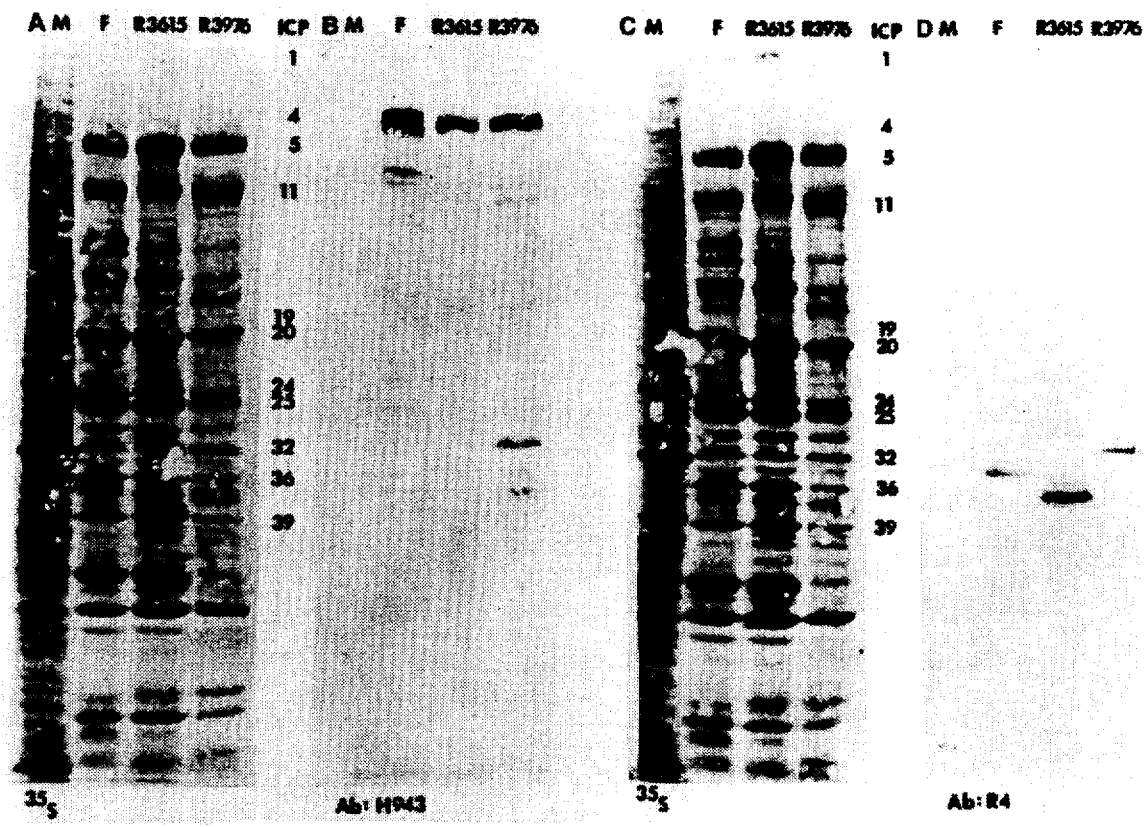
FIG. 4 is a photograph of autoradiographic images and a photograph of stained electrophoretic gels.

The results are illustrated in FIG. 4 wherein autoradiographic images (A and C) and photographs of lysates of cells mock infected or infected with HSV-1(F) or recombinants that were separated electrophoretically in denaturing gels, transferred electrically to a nitrocellulose sheet, and stained with monoclonal antibody H943 (B) or rabbit polyclonal antibody R4 (D) are presented. The numbers to the right of panels A and C indicate the infected-cell protein designations of Honess et al., *J. Virol.*, 12, 1347–1365 (1973) and Morse et al, *J. Virol.*, 26, 398–410 (1978).

Lysates of R3976-infected cells exhibited a band which reacted with both monoclonal antibody H943 and polyclonal rabbit serum R4 (FIG. 4). This band migrated more slowly than the band formed by lysates of HSV-1(F)-infected cells which reacted with R4 rabbit serum only. The band containing the truncated ICP34.5 protein reacted only with rabbit R4 serum and migrated faster than the authentic protein specified by HSV-1(F). These results provide definitive evidence supporting the existence of the open reading frame by showing that insertion of a foreign epitope into the gene in frame resulted in expression of both the predicted trimer Ala-Thr-Pro and the foreign epitope in the same protein. The repeated trimer must be in ICP34.5 and not in some other protein.

EXAMPLE 4

Immunization Routes, Dosages and Indications

A human host is preferably inoculated with a vaccine comprising an immunity-inducing dose of one or more of the live vaccinal recombinant strains of the invention by the parenteral route, preferably by intramuscular or subcutaneous injection. Also, inoculation may be effected by surface scarification, or by inoculation of a body cavity. Typically, one or several inoculations of between about 10 and 1,000,000 pfu each, as measured in susceptible human or nonhuman primate cell lines, are sufficient to effect immunization of a human host.

Indications for vaccination include:

a) a desire or need to boost the level of immunity of the host;

b) a lack of immunity in the face of a high probability of natural infection; or c) a lack of immunity and a likelihood that the subject will become immunologically compromised due to immunosuppressive therapy in the immediate or near future.

The vaccine according to the present invention may be conveniently utilized in liquid form or in freeze-dried form, in the latter case in combination with one or more suitable preservative and protective agents to protect the vaccinal strains during the freeze drying process.

To test the possible role of the infected cell protein 34.5 (ICP34.5), the product of the $\gamma_1 34.5$ gene, a series of four viruses were constructed. These viruses, schematically represented in FIGS. 5A–5C, were constructed using the procedures described by Post et al., *Cell*, 25,227 (1981) as follows.

EXAMPLE 5

Construction and Testing of Virus R4002

Rabbit skin cells of a convenient cell line (VERO cells available from the American Type Culture Collection may also be used) were cotransfected with intact DNA of HSV-1(F)Δ305 deposited with the American Type Culture Collection, 12301 Parklawn Drive, Rockville, Md. under accession number ATCC VR2279 a virus from which a portion of the tk gene was specifically deleted [Post et al., *Cell*, 227 (1981)], and with a fragment of plasmid pRB3615, which contains the α27-tk gene inserted into the BstEII site within the $\gamma_1 34.5$ gene contained in the BamHI S fragment. Recombinant virus of the tk$^+$ type were then selected and plaque-purified on human 143TK$^-$ cells in medium containing HAT hypoxanthine, aminopterin, and thymidine ("HAT Medium").

The fragment, including the α27-tk gene, contains a 5' non-transcribed promoter, a transcribed non-coding sequence, and an initiating methionine codon of the glycoprotein H gene downstream from the tk gene [Chou et al., *J. Virol.*, 57 629 (1986)]. The BstEII site into which the α27-tk fragment was inserted is immediately upstream of the codon 29 of the $\gamma_1 34.5$ open reading frame. As a consequence of the insertion, the initiating codon of glycoprotein H was fused in frame and became the initiating codon of the truncated open reading frame of the $\gamma_1 34.5$ gene as shown in the row of FIG. 5 identified as "Frame $\gamma_1 34.5$."

Figure 5A:
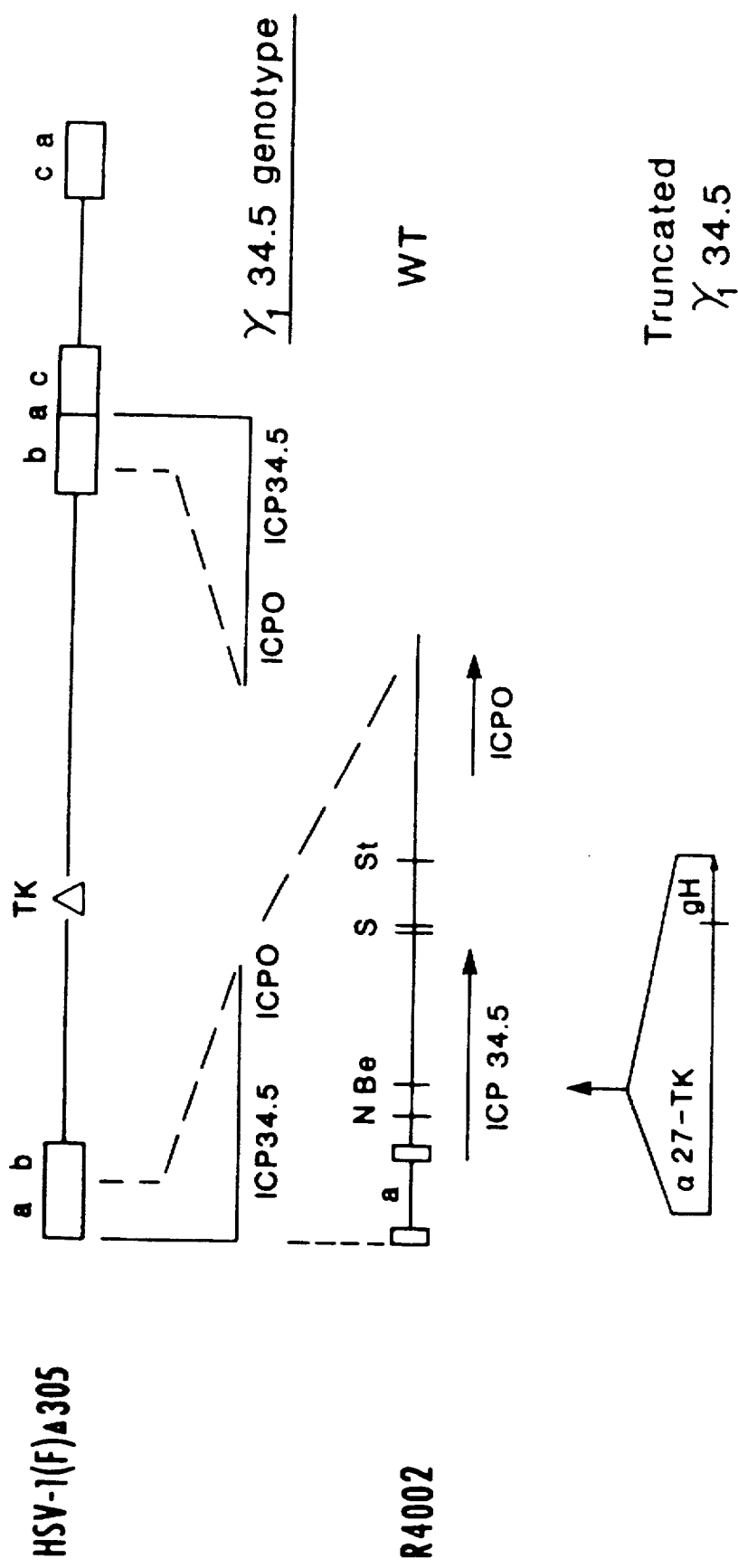

FIGS. 5A–5C is a schematic representation of the sequence arrangements of the genome of wild type strain HSV-1 strain F [HSV-1(F)] and of recombinant viruses derived from it. In FIGS. 5A and 5B, N, Be, S, St are abbreviations for NcoI, BstEIII, SacI and StuI restriction endonucleases (available from New England Biolabs, Beverly, Mass.), respectively. The numbers in parentheses are the tk$^+$ version of each construct tested in mice.

To the right of "HSV-1(F)Δ305" in FIG. 5A, is shown the sequence arrangement of a deletion mutant of HSV-1(F) deposited with the American Type Culture Collection, 12301 Parklawn Drive, Rockville, Md. under accession number ATCC VR2279 on Aug. 14, 1990. HSV-1 DNA consists of two components, long and short, each consisting of unique sequences flanked by inverted repeats. The open rectangles identify the inverted repeats ab, b'a'c, and ca [Wadsworth et al., *J. Virol.*, 15, 1487 (1975)]. The HSV-(F) a sequence consists of approximately 500 bp and is present in direct orientation at the two genomic termini and in the inverted orientation at the junction between the long and short two components, Wadsworth et al., supra. The b and c sequences are approximately 9 and 6 Kbp long, respectively, Wadsworth et al., supra. The triangle marked "TK" identifies the position of the tk gene and of the BglII-SacI sequence of BamHI Q fragment deleted from HSV-1(F)Δ305.

In FIG. 5A, the lines to the left of "$\gamma_1$34.5 genotype" and to the left of "WT," show that the b sequences contain the gene specifying ICP34.5 and ICP0 and, since the b sequence is repeated in an inverted orientation, there are two copies of these genes per genome. The construction of the α27-tk fragment containing portions of the glycoprotein H gene (shown to the left of "truncated $\gamma_1$34.5") is described in Chou et al., *J. Virol.*, 57, 629 (1986); Ackermann et al., *J. Virol.*, 58, 843 (1986); and Chou et al., *J. Virol.*, 64, 1014 (1990)]. The construction of pRB3615 is described in Chou et al., *J. Virol.*, 57, 629 (1986).

Of 20 tk$^+$ recombinant viruses screened, two were found to specify only the predicted truncated product of the chimeric $\gamma_1$34.5 gene and one, designated as R4002, was analyzed for the presence of the α27-tk gene insert in both copies of the $\gamma_1$34.5 gene. Plasmids and viral DNAs were digested with BamHI or, in case of the R4009, with both BamHI and SpeI. A fragment NcoI to SphI contained entirely within the coding sequences of $\gamma_1$34.5 (left panel) and the BamHI Q fragment of HSV-1(F) (right panel) were used as hybridization probes. The probes were labeled by nick translation of the entire plasmid DNAs with [α-$^{32}$] dCTP and reagents provided in a kit by New England Nuclear (Boston, Mass.). DNAs limit-digested with BamHI or both BamHI and SpeI were electrophoretically separated on 0.8% agarose gels in 90 mM Tris-Phosphate buffer at 40 V overnight. The DNA was then transferred by gravity to two nitrocellulose sheets sandwiching the gel and hybridized overnight with the respective probes.

Figure 6:
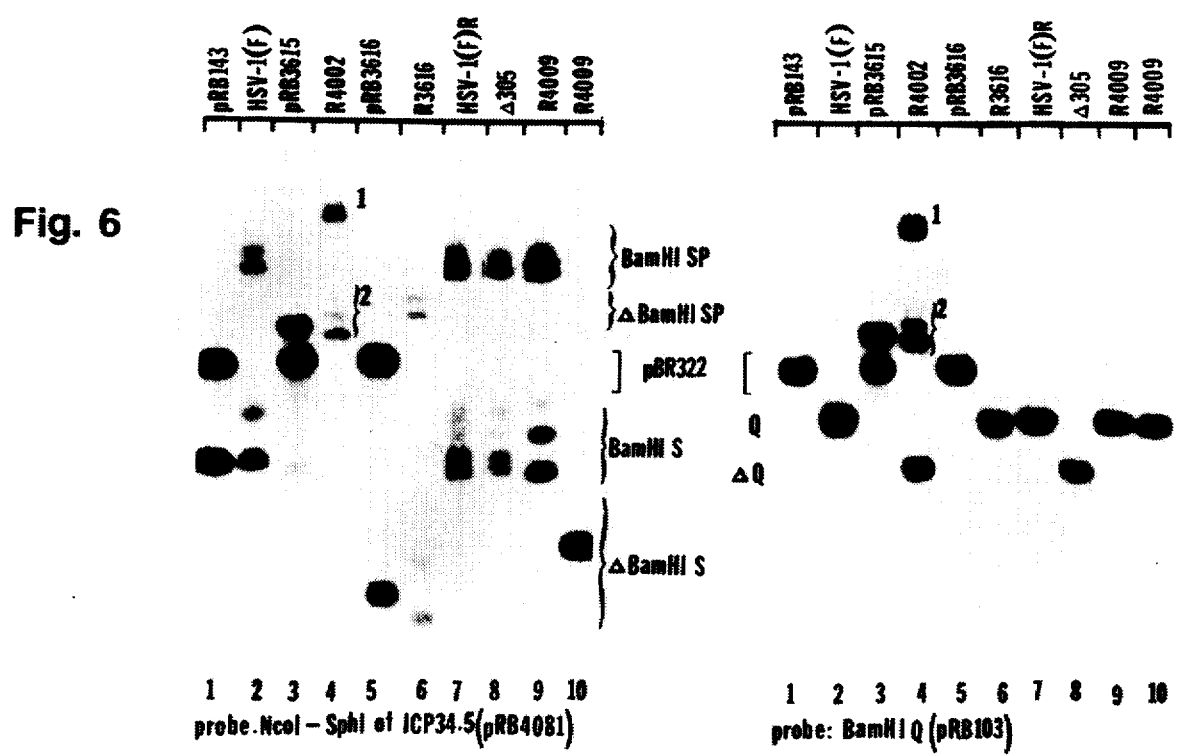
FIG. 6 is a photographic reproduction of an autoradiographic image of electrophoretically-separated digests of plasmid, viral and mutant viral DNA.

FIG. 6 is a photographic reproduction of an autoradiographic image of electrophoretically separated digests of plasmid, wild type and mutant virus DNA, transferred to a solid substrate and hybridized with the labeled probes for the presence of $\gamma_1$34.5 and tk genes. Results for DNA digested with BamHI are shown in the left panel (except for lane 10), while results for DNA digested with BamHI and SpeI are shown in the left panel, lane 10, and in the right panel of FIG. 6.

$\gamma_1$34.5 maps in BamHI S and SP fragments which form a characteristic ladder of bands at 500 base pair increments. The ladders are a consequence of the variable number of a sequences in the repeats flanking the unique sequences of the L component. Inasmuch as BamHI cleaves the viral genome within the inverted repeats but not at the junction between the L and S components, BamHI S is the terminal fragment of the viral genome at the terminus of the long component, whereas BamHI SP is a fragment formed by the fusion of the terminal BamHI P, the terminal BamHI fragment of the short component. Bands of BamHI S and its deleted version (ΔBamHI S), BamHI SP and ΔBamHI SP, and BamHI Q and ΔBamHI Q are indicated.

In FIG. 6, band 1 represents the 1.7 Kbp α27-tk insert into the BamHI SP fragment in R4002 and therefore this fragment reacted with both labeled probes (lanes numbered 4 in both panels). Band 2 represents the same insertion into the BamHI S fragment.

As indicated in the fourth lanes of FIG. 6, left and right panels, the α27-tk gene is inserted in both copies (designated 1 and 2 next to bands in the fourth lanes) of the $\gamma_1$34.5 gene.

Lysates of cells were infected with HSV-1(F) or "mock infected" by exposure to Medium 199V for the same amount and recombinant viruses were separated electrophoretically in denaturing polyacrylamide (10%) gels, transferred electrically to a nitrocellulose sheet, and stained with rabbit polyclonal antibody R4 described elsewhere [Ackermann et al., *J. Virol.*, 58, 843 (1986) and Chou et al., *Cell*, 41, 803 (1985)]. Replicate cultures of Vero cells were infected and labeled with [$^{35}$-S]methionine (New England Nuclear, Boston, Mass.) from 12 to 24 hours post infection. The procedures were as described [Ackermann et al., *J. Virol.*, 58, 843 (1986) and Chou et al., *J. Virol.*, 64, 1014 (1990)] except that the bound antibody was made apparent with the alkaline phosphatase substrate system supplied by Promega Inc. (Madison, Wis.).

Figure 7:
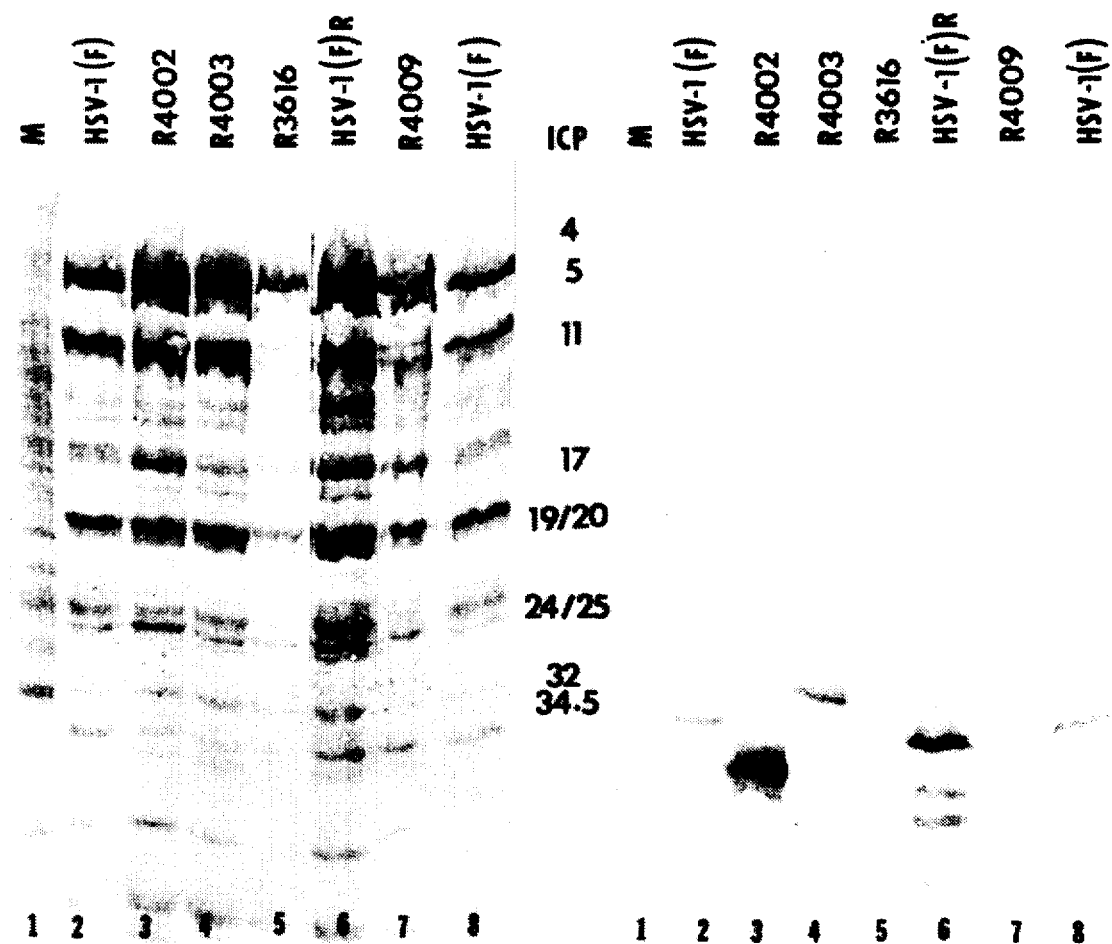
FIG. 7 is a photographic reproduction of an autoradiographic image in the right panel, and a photograph of a stained gel in the left panel, both being depictions of denaturing gel electrophoresis of cell lysates.

The results are illustrated in FIG. 7, the left panel of which is a photographic reproduction of an autoradiographic image, and the right panel of which is a photograph of an alkaline phosphatase gel (as described above). Infected cell proteins were designated by number according to Honess et al., *J. Virol.*, 12, 1346 (1973). Also shown is that this virus specifies only the truncated form of ICP34.5 (See in FIG. 7 right panel, lane 3, a single, fast migrating band for ICP34.5). The amounts of the native ICP34.5 protein detected in these and previous studies were generally low [Ackermann et al., *J. Virol.*, 58, 843 (1986)]. The chimeric genes formed by the fusion of the 5' transcribed non-coding region and the initiating codon of glycoprotein H in frame with the truncated $\gamma_1$34.5 gene were expressed far more efficiently than the native genes.

As illustrated in FIG. 5A, in the lines to the left of "WT" and "Truncated $\gamma_1$34.5," recombinant virus R4002 contains a thymidine kinase (tk) gene driven by the promoter of the α27 gene (α27-tk) is inserted in both copies of the ICP34.5 coding sequences.

This is shown in FIG. 7, lane 3, where only the band, the band corresponding to a truncated ICP34.5 appears, demonstrating that all ICP34.5 is made in those cells from a truncated gene. R4002 was used as a parent strain to generate other recombinant viruses used.

EXAMPLE 6

Construction and Testing of Viruses R3616 and R3617

A recombinant virus R3617 (as illustrated by the line in FIG. 5B to the right of "R3617"), lacking 1 Kbp of DNA in each copy of the $\gamma_1$34.5 gene, was generated by co-transfecting rabbit skin cells with intact R4002 DNA and the DNA of plasmid pRB3616. In plasmid pRB3616, the sequences containing most of the coding domain of $\gamma_1$34.5, i.e., those located between BstEII and StuI sites within the BamHI S fragment of HSV-1 strain F, had been deleted (FIG. 5B top). To generate pRB3616, plasmid pRB143 [Post et al., *Proc. Nat'l. Acad. Sci. (USA)*, 77, 4201 (1980)] was digested with BstEII and StuI, blunt-ended with T4 polymerase, and religated.

The progeny of the transfection were plated on 143TK$^-$ cells overlaid with medium containing BUdR to select for tk$^-$ viruses. Because the tk gene is present in both copies of the $\gamma_1$34.5 gene in R4002, the selected progeny of the transfection contain deletions in both copies. The selected tk$^-$ virus, designated as R3617, was analyzed for the presence of the deletion in both copies of the $\gamma_1$34.5 gene (data not shown). The $\gamma_1$34.5 gene was not present. See, e.g., FIG. 6, for R3616 where the tk gene is present in one copy at the normal position after repair.

For assays of neurovirulence, the deletion in the native tk⁻ gene of R3617, which traces its origin from HSV-1(F)Δ305, was repaired. This was done by cotransfection of rabbit skin cells with intact R3617 DNA and a BamHI Q fragment containing the tk gene. The virus selected for tk⁺ phenotype in 143TK⁻ cells was designated as R3616. This virus contains a wild type BamHI Q fragment (as shown in FIG. 6, right panel, lane 6) and does not make ICP34.5 (as shown in FIG. 6, right panel).

R3616 was deposited under accession number ATCC VR2280 with the American Type Culture Collection, 12301 Parklawn Drive, Rockville, Md. 20852 on Aug. 14, 1990.

EXAMPLE 7

Construction and Testing of Virus HSV-1(F)R

To ascertain that the phenotype of R3616 indeed reflects the deletion in the $\gamma_1 34.5$ gene, the $\gamma_1 34.5$ sequences deleted from R3616 were restored by cotransfecting rabbit skin cells with intact R3617 DNA, the HSV-1(F) BamHI Q DNA fragment containing the intact tk gene and the BamHI SP DNA fragment containing the intact $\gamma_1 34.5$ gene in the molar ratios of 1:1:10, respectively. Viruses of the tk⁺ type were then selected in 143TK⁻ cells overlaid with medium containing HAT. The tk⁺ candidates were then screened for the presence of wild type tk and $\gamma_1 34.5$ genes.

As expected, the selected virus designated as HSV-1(F)R schematically illustrated to the right of "HSV-1(F)R" in FIG. 5B contained a wild type (tk⁺) BamHI Q fragment (as shown by comparison of FIG. 6, right panel lanes 2 and 7), a wild type terminal L component fragment (as shown by comparison of FIG. 6, left panel lanes 2, 7, and 8), and expressed ICP34.5 as shown in FIG. 7, right panel, lane 6).

EXAMPLE 8

Construction of Virus R4010

To eliminate the possibility that the phenotype of R3616 reflects deletion in cryptic open reading frames, a virus was constructed to contain translational stop codons in all three reading frames in the beginning of ICP34.5 coding sequence. This virus was designated R4010, and is illustrated in FIG. 5B to the right of "R4010." A 20 base oligonucleotide containing translational stop codons and their complement sequences was constructed in an Applied Biosystems (Foster City, Calif.) 380D DNA synthesizer, mixed at equal molar ratio, heated to 80° C., and allowed to cool slowly to room temperature.

```
GTAACC T A GAC T A GTC T A GC*****

*****G A TCT G A TCA G A TCGCATTG
```

The asterisks (****) in this sequence, and in all sequences in FIG. 5C designate nucleotides from a vector plasmid that form cohesive ends with the synthesized oligomers. The annealed DNA was inserted into the HSV-1(F) BamHI S fragment at the BstEII site of the plasmid pRB143. The resulting plasmid pRB4009 contained a stop codon inserted in the beginning of the ICP34.5 coding sequence. The 20 mer DNA insertion also contained a SpeI restriction site which allowed rapid verification of the presence of the insert.

To generate the recombinant virus R4010, rabbit skin cells were cotransfected with the intact DNA of R4002 and the pRB4009 plasmid DNA. Recombinants of the tk⁻ type were selected in 143TK⁻ cells in medium containing BudR. The tk⁺ version of this virus, designated as R4009, was generated by cotransfection of intact tk⁻ R4010 DNA with HSV-1(F) BamHI Q DNA fragment, and selection of tk⁺ progeny. The virus selected for neurovirulence studies, R4009, contained the SpeI site in both BamHI S and SP fragments as shown by a comparison of FIG. 6, left panel, lanes 9 and 10) and did not express ICP34.5 as shown by FIG. 7, right panel lane 7).

R4009 was deposited under accession number ATCC VR2278 with the American Type Culture Collection, 12301 Parklawn Drive, Rockville, Md. 20852 on Aug. 14, 1990.

EXAMPLE 9

Construction and Testing of Virus R4004

R4004, FIG. 5C is a recombinant virus produced by insertion of a sequence encoding 16 amino acids, as illustrated in FIG. 7 to the right of "R4004." This sequence is the epitope of the monoclonal antibody H943 reactive with a viral protein designated as ICP4 [Hubenthal-Voss et al., *J. Virol.*, 62, 454 (1988)]. R4004 was generated by cotransfecting intact R4002 DNA and the DNA of plasmid pRB3976 containing the insert, and tk⁻ progeny were analyzed for the presence of the insert. The construction of recombinant plasmid pRB3976 is described elsewhere [Chou et al., *J. Virol.*, 57, 629 (1986) and Chou et al., *J. Virol.*, 64, 1014 (1990)] except that the sequence was inserted into both copies of the $\gamma_1 34.5$ gene rather than into a recombinant virus which had only one copy of the gene. This insertion merely truncates but does not inactivate the ICP34.5 protein.

That DNA encoding the epitope is inserted in both copies of the gene is shown in FIG. 7 by the coincident reactivity of the rabbit antibody to ICP34.5 at the band corresponding to ICP4. If the gene encoding the epitope were present in only one copy, two bands would be present.

For neurovirulence studies, the tk gene was restored to R4004 to form recombinant virus R4003 as described above. The DNA sequence was inserted in frame at the NcoI site at the initiating methionine codon of the $\gamma_1 34.5$ gene. The insert regenerated the initiating methionine codon and generated a methionine codon between the epitope and the remainder of ICP34.5.

The chimeric ICP34.5 specified by R4003 migrated more slowly in denaturing polyacrylamide gels (as seen in FIG. 7, right panel, lane 4) than the protein produced by other viruses illustrated in FIG. 7 because of the increased molecular weight due to the insertion of the epitope. The reactivity of the inserted epitope with monoclonal antibody H943 is reported elsewhere [Chou et al., *Cell*, 41, 803 (1985)] and is not shown here.

EXAMPLE 10

Culture and Neurovirulence Studies

Plaque morphology and size of all of the recombinants were similar to those of the wild type parent, HSV-1(F) when plated on VERO, 143TK⁻ and rabbit skin cell lines. Whereas HSV-1(F)R and R4003 replicated as well as the wild type virus in replicate cultures of Vero cells, the yields of R3616 and R4009 were reduced 3 to 4 fold.

Neurovirulence studies were done on female BalB/C mice obtained at 21 days of age (weight 9.4±1.8 gm) from Charles River Breeding Laboratories in Raleigh, N.C. The tk gene was restored in all recombinant viruses tested in mice.

Viruses HSV-1(F), R3617, HSV-1(F)R, R4009 and R4003 were diluted in minimal essential medium containing Earle's salts and 10% fetal bovine serum, penicillin and gentamicin. The mice were inoculated intracerebrally into the right cerebral hemisphere with dilutions of virus using a 26-gauge needle. The volume delivered was 0.03 ml, and each dilution of virus was tested in groups of 10 mice. The animals were checked daily for mortality for 21 days. The $LD_{50}$ was calculated with the aid of the "Dose Effect Analysis" computer program for Elevier Biosoft, Cambridge, United Kingdom. The results indicate the comparative ability of wild type and recombinant viruses to cause death after intracerebral inoculation of mice as provided in Table 1.

TABLE 1

| Virus in The Inoculum | Genotype | pfu/LD$_{50}$ |
|---|---|---|
| HSV-1(F) | Wild type parent virus | 420 |
| R3616 | 1000 bp deletion in the $\gamma_1 34.5$ | >1,200,000 |
| HSV-1(F)$_r$ | restoration of $\gamma_1 34.5$ and tk | 130 |
| R4009 | Stop codon in $\gamma_1 34.5$ | >10,000,000 |
| R4003 | Monoclonal antibody epitope inserted at the N terminal | 4,200 |

Although ICP34.5 was not essential for growth of HSV-1 in cells in culture, the results of the studies shown in Table 1 indicate that the deletion or termination of translation of the $\gamma_1 34.5$ had a very profound effect on the virulence of the virus. Thus, all of the mice inoculated with the highest concentration of R3616 survived. In the case of R4009, only 3 of 10 mice died as a result of inoculation with the highest concentration of virus. Virus HSV-1(F)R, in which the $\gamma_1 34.5$ gene was restored, exhibited the virulence of the parent virus.

The wild type virus and all of the recombinants have identical surface glycoproteins necessary for attachment and penetration into brain cells. Injection of $10^6$ pfu into the brain should result in infection and death of a significant number of the brain cells. Death following intracerebral inoculation results from viral replication, spread from cell to cell, and cell destruction before the immune system has a chance to act. Titrations of brain tissue suspended in minimal essential medium containing Eagle's salts and 10% fetal calf serum showed that the brains of animals inoculated with the viruses which failed to make ICP34.5 contained very little virus. Thus, for the R3616 and R4009 viruses, the recovery was 120 and 100 pfu per gram of brain tissue, respectively. In contrast, the amounts of virus recovered from mice inoculated with HSV-1(F)R and R4003 were $6 \times 10^6$ and $4 \times 10^6$, respectively. These results indicate that the failure of the two recombinant viruses to cause death must be related to poor spread of virus in neuronal tissue, and this may be a reflection of the inability of mutant viruses to replicate in the central nervous system (CNS).

As a general principle, all deletion mutants in coding sequences generated and tested to date [Meignier et al., J. Infect. Dis., 158 602 (1988) and Meignier et al., Virology, 162, 251 (1987)] have a reduced capacity to cause disease in experimental animals. None of the HSV-1 mutants unambiguously carrying a deletion in a single gene, however, exhibits as drastic a decrease in ability to cause death in experimental animals as those according to the present invention.

The loss of capacity to replicate in the CNS and cause death is not due to rearrangement of DNA as a consequence of the deletion. Identical loss of capacity to replicate in the CNS was obtained by insertion of the stop codons. Furthermore, the loss of virulence by the mutants containing the stop codons was not a consequence of some rearrangement of the DNA sequences at the terminus of the genome since insertion of the ICP4 epitope, a much larger insert, into the coding sequence had a marginal effect on the ability of the virus to replicate in the CNS. These data also indicate that the modification of the N terminus of the protein did not grossly debilitate the capacity of the protein to function in the mouse brain. While the function of ICP34.5 is not known, it is not essential for growth in cells in culture. The slight decrease in replication of this virus in cells in culture is not concordant with the loss of its ability to multiply and destroy the CNS in mice. The failure to recover virus from the CNS suggests that brain cells do not express genes whose products can substitute for $\gamma_1 34.5$ gene product and complement the deletion mutants. ICP34.5 extends the host range of HSV-1 and enables the virus to replicate in the CNS. From this point of view, the protein is necessary for the dissemination of the virus from cell to cell and destruction of brain tissue characteristic of human encephalitis.

Gross deletions in a viral genome are reported to result in decreased capacity to cause death in experimental animals [Centifanto-Fitzgerald et al., J. Exp. Med., 155, 475 (1982) and Meignier et al., J. Infect. Dis., 158, 602 (1988)]. In the above examples, rearrangements in the viral genome, insertion of non-homologous DNA, and deletion of cryptic open reading frames as the cause of the loss of neurovirulence have been excluded as the bases for this decreased capacity. The above examples directly relate the capacity to replicate in CNS, the hallmarks of neurovirulence, to the synthesis and expression of a specific protein made in relatively non-abundant amounts and not essential for replication in cultured cells. By its properties, the product of the $\gamma_1 34.5$ gene comes closest of all known viral proteins to the definition of an HSV neurovirulence factor.

EXAMPLE 11

Latency Studies

Five Balb/c mice in each of 4 groups were anesthetized, a cornea was scarified using a hypodermic needle, and the cornea was bathed in a viral suspension of $1\times10^7$ pfu or $1\times10^8$ pfu of virus as indicated in Table 2. At 28 days post infection the trigeminal ganglia were removed from anesthetized and exsanguinated mice. The ganglia were pooled from each mouse, cut into small pieces and incubated for 3–4 days before plating on VERO cells. Plaques were counted 3 days later, with results as shown in Table 2.

TABLE 2

| | $1 \times 10^7$ PFU | | $1 \times 10^8$ PFU | |
|---|---|---|---|---|
| Virus Strains | Mouse # | PFU recovered from ganglia | Mouse # | PFU recovered from ganglia |
| Parental | 1 | $3 \times 10^3$ | 1 | dead-day 13 |
| | 2 | $3 \times 10^1$ | 2 | $2.5 \times 10^2$ |
| | 3 | $4 \times 10^3$ | 3 | $1.9 \times 10^3$ |
| | 4 | $5 \times 10^1$ | 4 | $1 \times 10^2$ |
| | 5 | $2 \times 10^2$ | 5 | 0 |
| Deletion | 1 | 0 | | |
| | 2 | 0 | | |
| | 3 | 0 | | |
| | 4 | 0 | | |
| | 5 | 0 | | |

TABLE 2-continued

| Virus Strains | 1 × 10⁷ PFU | | 1 × 10⁸ PFU | |
|---|---|---|---|---|
| | Mouse # | PFU recovered from ganglia | Mouse # | PFU recovered from ganglia |
| Stop Codon | 1 | 0 | 1 | 0 |
| | 2 | 0 | 2 | 0 |
| | 3 | 0 | 3 | 0 |
| | 4 | 0 | 4 | 0 |
| | 5 | 0 | 5 | 0 |
| Restored | 1 | $4 \times 10^1$ | 1 | $1.4 \times 10^3$ |
| | 2 | $1 \times 10$ | 2 | $1.2 \times 10^3$ |
| | 3 | 0 | 3 | $1 \times 10^2$ |
| | 4 | 0 | 4 | $5 \times 10^1$ |
| | 5 | 0 | 5 | $1.8 \times 10^3$ |

The results presented in Table 2 show that HSV viruses having a deletion in or stop codon inserted in the ICP34.5 gene poorly establish latency or do not reactivate.

Although the present invention has been described in terms of an HSV-1 construction, the ICP34.5 gene of HSV-2 may be modified according to the present invention. Although no gene is reported to be identified in the region of the deletion, Taha et al., *J. Gen. Virol.*, 70, 3073–3078 (1989), reports a variant of HSV-2 strain HG52 having a deletion of 1.5 kbp including the domain of the gene that specified ICP34.5. The virus grows but is completely avirulent (50% lethal dose, >10⁷ PFU) in mice inoculated intracerebrally. Therefore, an HSV-2 virus which lacks an ICP34.5 gene encoding an active gene product may be produced according to the present invention just as in an HSV-1 virus according to the present invention, by insertion of a stop codon, or by a small deletion or insertion in the coding region of the ICP34.5 gene as determined by its homology to the HSV-1 ICP34.5 gene.

In addition to utility in immunizing a human host against wild type HSV-1 and HSV-2, the virus strains of the invention are believed to have utility in treating a subject infected with wild type HSV. Treatment can be effected using similar dosages and routes of administration as used in immunization, described above.

The foregoing detailed description is given for clearness of understanding only, and no unnecessary limitations are to be understood or inferred therefrom, as modifications within the scope of the invention will be obvious to those skilled in the art.

I claim:

1. A recombinant herpes simplex virus genome having modified $\gamma_1 34.5$ genes incapable of expressing an active ICP34.5 gene product, wherein the modification is selected from the group consisting of insertions, substitutions, and deletions wherein the deletions have at least one terminus within the $\gamma_1 34.5$ genes.

2. The herpes simplex virus genome of claim 1 wherein each said $\gamma_1 34.5$ gene comprises a stop codon in reading frame between a first and a last codon of a coding sequence of said $\gamma_1 34.5$ gene.

3. The herpes simplex virus genome of claim 2 wherein said virus is HSV-1(F) and at least one said $\gamma_1 34.5$ gene comprises said stop codon at a BstEII restriction endonuclease site therein.

4. The herpes simplex virus genome of claim 1 wherein at least one modified $\gamma_1 34.5$ gene comprises a deletion mutation.

5. The herpes simplex virus genome of claim 4 wherein said herpes simplex virus genome is HSV-1(F) and said deletion mutation comprises a portion of a coding sequence between BstEII and StuI restriction endonuclease sites therein.

6. The herpes simplex virus genome of claim 1 wherein said virus is HSV-1.

7. The herpes simplex virus genome of claim 1 wherein said virus is HSV-2.

8. A vaccine comprising a herpes simplex virus genome having modified $\gamma_1 34.5$ genes incapable of expressing an active ICP34.5 gene product, and a pharmaceutically acceptable diluent, adjuvant or carrier, wherein the modification is selected from the group consisting of insertions, substitutions, and deletions wherein the deletions have at least one terminus within the $\gamma_1 34.5$ genes.

9. The vaccine of claim 8 wherein each said $\gamma_1 34.5$ gene comprises a stop codon in reading frame between a first and a last codon of a coding sequence of said $\gamma_1 34.5$ gene.

10. The vaccine of claim 4 wherein said virus is HSV-1(F) and at least one said $\gamma_1 34.5$ gene comprises said stop codon at a BstEII restriction endonuclease site therein.

11. The vaccine of claim 8 wherein at least one said $\gamma_1 34.5$ gene comprises a deletion mutation.

12. The vaccine of claim 11 wherein said virus is HSV-1(F) and said deletion mutation comprises a portion of a coding sequence between BstEII and StuI restriction endonuclease sites therein.

13. The vaccine of claim 8 wherein said virus is HSV-1.

14. The vaccine of claim 8 wherein said virus is HSV-2.

15. A method of immunizing a host against a herpes simplex virus comprising the step of inoculating said host with an immunity-inducing dose of a vaccine comprising a herpes simplex virus genome having modified $\gamma_1 34.5$ genes incapable of expressing an active ICP34.5 gene product and a pharmaceutically acceptable diluent, adjuvant, or carrier, wherein the modification is selected from the group consisting of insertions, substitutions, and deletions wherein the deletions have at least one terminus within the $\gamma_1 34.5$ genes.

16. The method of claim 15 wherein each said $\gamma_1 34.5$ gene has a stop codon in reading frame between a first and a last codon of a coding sequence of said $\gamma_1 34.5$ gene.

17. The method of claim 16 wherein said virus is HSV-1(f) and at least one said $\gamma_1 34.5$ gene comprises said stop codon at a BstEII restriction endonuclease site therein.

18. The method of claim 15 wherein at least one modified $\gamma_1 34.5$ gene comprises a deletion mutation.

19. The method of claim 18 wherein said virus is HSV-1(F) and said deletion mutation comprises a portion of a coding sequence between BstEII and StuI restriction endonuclease sites therein.

20. The method of claim 15 wherein said virus is HSV-1.

21. The method of claim 15 wherein said virus is HSV-2.

22. A method of preparing a vaccine comprising the steps of: modifying the $\gamma_1 34.5$ genes of a herpes simplex virus, to render said genes incapable of expressing an active ICP34.5 gene product; and combining said virus with a pharmaceutically acceptable diluent, adjuvant, or carrier, wherein the modification is selected from the group consisting of insertions, substitutions, and deletions wherein the deletions have at least one terminus within the $\gamma_1 34.5$ genes.

23. The method of claim 22 wherein said modifying step comprises the step of inserting a stop codon in reading frame between a first and a last codon of a coding sequence of said $\gamma_1 34.5$ genes.

24. The method of claim 23 wherein said virus is HSV-1(F) and said inserting step comprises the step of introducing a stop codon at a BstEII restriction endonuclease site in the $\gamma_1 34.5$ genes thereof.

25. The method of claim 22 wherein said modifying step comprises the step of deleting a portion of said $\gamma_1 34.5$ genes.

26. The method of claim 25 wherein said virus is HSV-1(F) and said deleting step comprises the step of deleting a portion of a coding sequence between BstEII and StuI restriction endonuclease sites therein.

27. The method of claim 22 wherein said virus is HSV-1.

28. The method of claim 22 wherein said virus is HSV-2.

* * * * *